(12) United States Patent
Yang

(10) Patent No.: US 8,333,972 B2
(45) Date of Patent: Dec. 18, 2012

(54) UNCONVENTIONAL ANTIGEN TRANSLATED BY A NOVEL INTERNAL RIBOSOME ENTRY SITE ELICITS ANTITUMOR HUMORAL IMMUNE REACTIONS

(75) Inventor: Xiao-Feng Yang, Huntingdon Valley, PA (US)

(73) Assignee: Temple University, Philadelphia, PA (US)

( * ) Notice: Subject to any disclaimer, the term of this patent is extended or adjusted under 35 U.S.C. 154(b) by 783 days.

(21) Appl. No.: 12/377,444

(22) PCT Filed: Aug. 16, 2007

(86) PCT No.: PCT/US2007/076088
§ 371 (c)(1),
(2), (4) Date: Feb. 13, 2009

(87) PCT Pub. No.: WO2008/022253
PCT Pub. Date: Feb. 21, 2008

(65) Prior Publication Data
US 2010/0136036 A1    Jun. 3, 2010

Related U.S. Application Data

(60) Provisional application No. 60/822,580, filed on Aug. 16, 2006.

(51) Int. Cl.
| | |
|---|---|
| A61K 39/00 | (2006.01) |
| C07H 21/00 | (2006.01) |
| C12N 15/12 | (2006.01) |
| C12N 15/63 | (2006.01) |
| C12N 5/00 | (2006.01) |
| C12N 1/00 | (2006.01) |
| C07K 14/00 | (2006.01) |
| C07K 16/00 | (2006.01) |
| C12Q 1/68 | (2006.01) |
| C12Q 1/02 | (2006.01) |
| G01N 33/535 | (2006.01) |
| G01N 33/53 | (2006.01) |
| G01N 33/68 | (2006.01) |
| A61P 37/04 | (2006.01) |

(52) U.S. Cl. .................. 424/185.1; 530/350; 530/387.9; 424/184.1

(58) Field of Classification Search .................. None
See application file for complete search history.

(56) References Cited

U.S. PATENT DOCUMENTS

2004/0031072 A1   2/2004  La Rossa et al.
2005/0287544 A1   12/2005 Bertucci et al.

OTHER PUBLICATIONS

Greenspan et al. (Nature Biotechnology 7: 936-937, 1999).*
Saiz, J.C. et al., Internal initiation of translation efficiency in different heptatis C genotypes isolated from interferon treated patients, Arch Virol. 1999, 144(2): 215-29.
Monji, M., et al., Identification of a novel human cancer/testis antigen, KM-HN-1, recognized by cellular and humoral immune responses, Clin. Cancer Res. Sep. 15, 2004:10 (18 Pt. 1): 6047-57.
Certa, U. et al., Expression modes of interferon-alpha inducible genes in sensitive and resistant human melanoma cells stimulated with regular and pegylated interferon-alpha, Gene, Oct. 2, 2003: 315:79-86.
Yang, et al., CML66, a broadly immunogenic tumor antigen, elicits a humoral immune response associated with remission of chronic myelogenous leukemia, Proc. Natl. Acad. Sci U.S.A. Jun. 19, 2001; 98(13): 7492-7.
Hellen, C.U. et al., Internal ribosome entry sites in eukaryotic mRNA molecules, Genes Dev. Jul. 1, 2001; 15(13); 1593-612, Review, No abstract available.
Xiong, Z. et al., An unconventional antigen translated by a novel internal ribosome entry site elecits antitumor humoral immune reactions, J. Immunol. Oct. 1, 2006; 177(7); 4907-16.
International Search Report, PCT/US07/76088 dated Aug. 16, 2007.

* cited by examiner

*Primary Examiner* — Robert A Zeman
(74) *Attorney, Agent, or Firm* — Caesar, Rivise, Bernstein, Cohen & Pokotilow, Ltd.

(57) ABSTRACT

The invention provides a novel antigen, MPD6, which belongs to the group of cryptic antigens without conventional genomic structure and is encoded by a cryptic open reading frame located in the 3' untranslated region (3'UTR) of myotrophin mRNA. MPD6 elicits IgG antibody responses in a subset of PV patients, as well as patients with chronic myelogenous leukemia and prostate cancer. The translation of MPD6 was mediated by a novel internal ribosome entry site (IRES) upstream of the MPD6 reading frame. Furthermore, the MPD6-IRES mediated translation, but not myotrophin-MPD6 transcription, was significantly upregulated in response to IFN-α stimulation. These findings demonstrate that a novel IRES-mediated mechanism is responsible for the translation of unconventional self-antigen MPD6 in responsive to IFN-α stimulation. The eliciting anti-tumor immune response against unconventional antigen MPD6 in patients with myeloproliferative diseases indicates MPD6 as a target of novel immunotherapy.

3 Claims, 11 Drawing Sheets

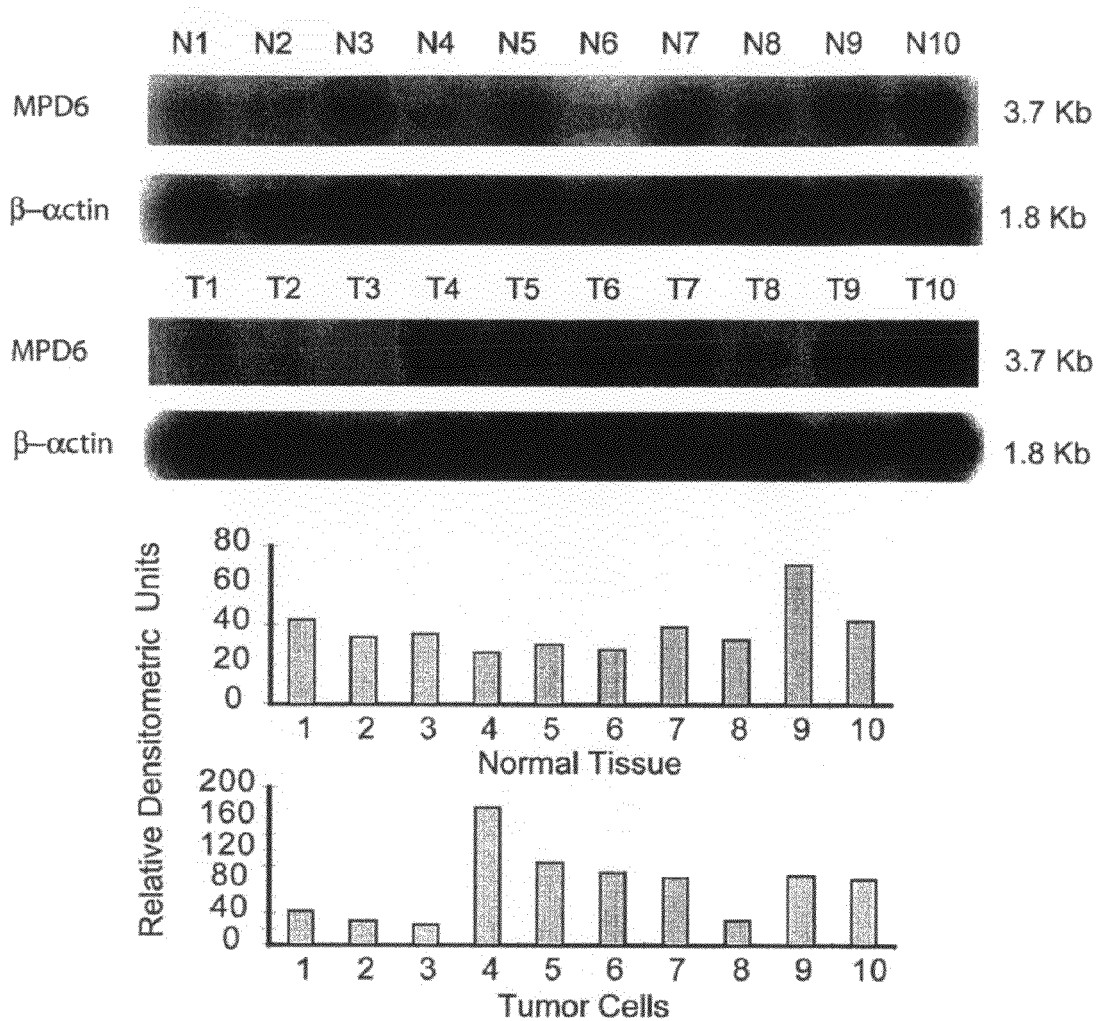

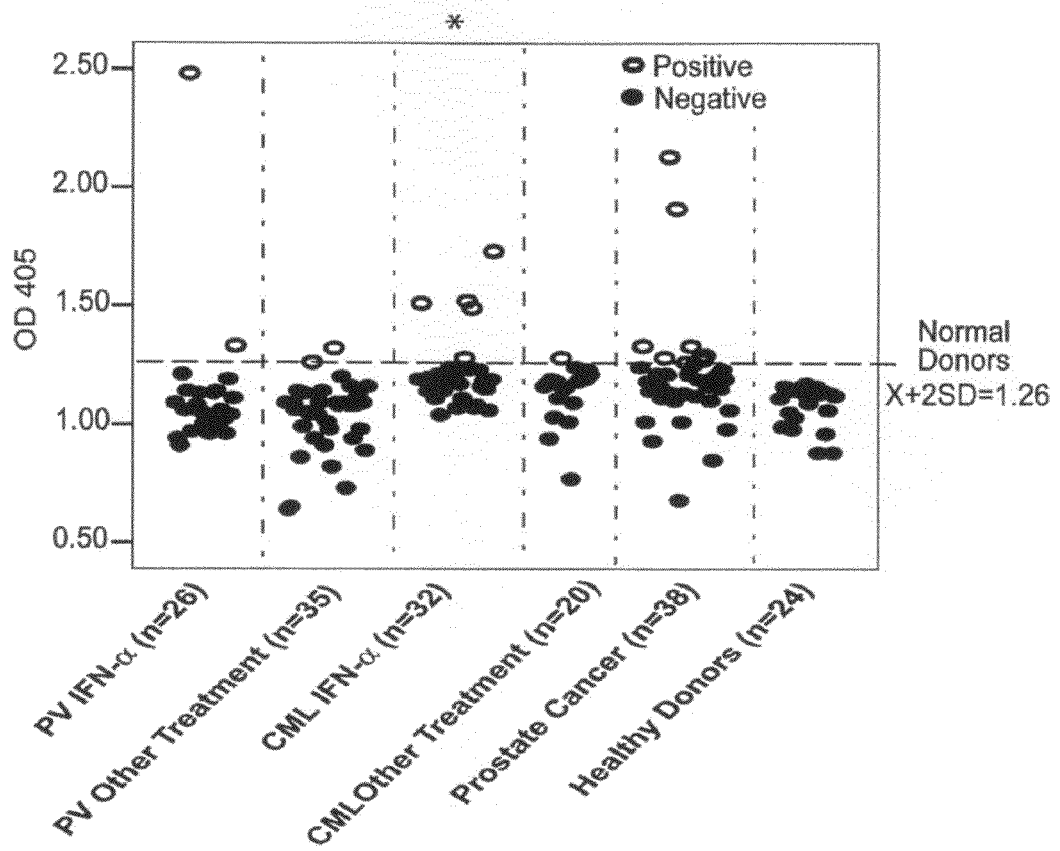

MPD6-IRES Region (380 bases)
Free Energy = -77.2 (kcal/mol)

EMCV-IRES Control (293 bases)
Free energy = -112.9 (kcal/mol)

XIAP-IRES Control (210 bases)
Free energy = -36.31 (kcal/mol)

MPD6-IRES Region (380 bases) Free Energy = -90.39 (kcal/mol)

EMCV-IRES Control (293 bases)
Free energy = -123.34 (kcal/mol)

XIAP-IRES Control (210 bases)
Free energy = −44.69 (kcal/mol)

UNCONVENTIONAL ANTIGEN TRANSLATED BY A NOVEL INTERNAL RIBOSOME ENTRY SITE ELICITS ANTITUMOR HUMORAL IMMUNE REACTIONS

CROSS-REFERENCE TO RELATED APPLICATIONS

This application claims benefit of U.S. Provisional Patent Application No. 60/822,580, filed Aug. 16, 2006.

STATEMENT REGARDING FEDERALLY SPONSORED RESEARCH OR DEVELOPMENT

This invention was made with government support under NIH Grant No. AI054514 awarded by the National Institutes of Health. The government has certain rights in the invention.

BACKGROUND OF THE INVENTION

1. Field of Invention

This invention relates to self-tumor antigens and methods and compositions to generate immunity in humans against self tumor antigens. This invention is more particularly related to eliciting or enhancing immunity against human self tumor antigen encoded by unconventional reading frames with homology to foreign proteins 2. Description of Related Art Self-tumor antigens that elicit anti-tumor immune responses in responses to interferon-α (IFN-α) stimulation remain poorly defined. Currently, most of tumor antigens and autoantigens are encoded by primary open reading frames in mRNAs.

A new generation of tumor antigens has been defined as "self proteins" (J. Exp. Med. 180:1-4, 1994; Cell 82:13-17, 1995). Self tumor antigens are proteins that are expressed by both normal cells and cancer cells. (As opposed to mutated proteins that are unique and thus cancer specific.) Self tumor antigens are typically overexpressed by the cancer cells. Certain self proteins, such as HER-2/neu and c-myc, are known to be involved in malignant transformation. See U.S. Patent Publication No. 20020019331 to Cheever.

Internal ribosome entry site associated studies have been extensive in biochemistry field but not immunology fields, e.g., tumor immunology field. The practical use of internal ribosome entry site is limited in construction of bicistronic vectors for gene therapy and construction of bicistronic vectors for gene expression.

Due to the difficulties in the current approaches to treatment and prevention of cancer, there is a need in the art for improved methods and compositions. The present invention fulfills this need, and further provides other related advantages.

All references cited herein are incorporated herein by reference in their entireties.

BRIEF SUMMARY OF THE INVENTION

The inventor screened a human testis cDNA library with sera from three polycythemia vera (PV) patients who responded to IFN-α and identified a novel antigen, MPD6. MPD6 belongs to the group of cryptic antigens without conventional genomic structure and is encoded by a cryptic open reading frame located in the 3' untranslated region (3'UTR) of myotrophin mRNA. MPD6 elicits IgG antibody responses in a subset of PV patients, as well as patients with chronic myelogenous leukemia and prostate cancer, suggesting that it is broadly immunogenic. The expression of myotrophin-MPD6 transcripts in tumor cells was upregulated in some tumor cells, but only slightly increased in K562 cells in response to IFN-α treatment. By using bicistronic reporter constructs, the inventor showed that the translation of MPD6 was mediated by a novel internal ribosome entry site (IRES) upstream of the MPD6 reading frame. Furthermore, the MPD6-IRES mediated translation, but not myotrophin-MPD6 transcription, was significantly upregulated in response to IFN-α stimulation. These findings demonstrate that a novel IRES-mediated mechanism is responsible for the translation of unconventional self-antigen MPD6 in responsive to IFN-α stimulation. The eliciting of an anti-tumor immune response against unconventional antigen MPD6 in patients with myeloproliferative diseases indicates MPD6 as a target of novel immunotherapy.

Taken together, the results indicate that the novel IRES-mediated translation of the unconventional cryptic antigen peptide of MPD6, but not transcription of RNA transcripts, is increased by IFN-α, which may provide a novel mechanism underlying of the expansion of self-antigen repertoire that mediates both autoimmune as well as anti-tumor immune responses.

This invention is the first demonstration that a novel unconventional self-tumor antigen encoded in the 3' untranslated region (3'UTR), and translated by internal ribosome entry site can elicit anti-tumor humoral immune responses. This discovery has significantly improved the understanding of how host immune system could expand self antigen repertoire and functional significance of secondary open reading frame in mRNAs in expansion of human proteome.

The MPD6 antigen can elicit anti-tumor IgG antibody responses, potentially T cell responses. Expression of this unconventional antigen is upregulated in responses to interferon-α (IFN-α) stimulation; therefore, this antigen can be used for diagnosis, prognosis and immunotherapy for viral infections, inflammation, autoimmune diseases and tumors.

The invention was driven by the desire to develop a new unconventional self-tumor antigen broadly immunogenic in patients with polycythemia vera, which is myeloproliferative disease, chronic myelogenous leukemia and prostate cancer, etc. This unconventional self-tumor antigen can be used for diagnosis and prognosis, as well as the target for future immunotherapy.

This invention is also the first report showing that anti-tumor immune responses, elicited by unconventional self-tumor antigen, may lead to tumor remission. The inventor discovered that autoimmune diseases associated with interferon-α therapy may be contributed by unconventional self-tumor antigens. Immune responses to MPD6 unconventional self-tumor antigen can be targeted for the purposes of diagnosis, prognosis and immunotherapy for viral infections, inflammation, autoimmune diseases and tumors.

The unconventional self-tumor antigen(s) encoded in the 3' untranslated region and translated by internal ribosome entry site can elicit humoral and T cell immune responses that are useful for diagnosis, prognosis, and therapy for viral infections, inflammation, autoimmune diseases and tumors. The MPD6 internal ribosome entry site can be used for construction of bicistronic gene therapy vectors or other eukaryotic expression vectors for gene expression in biomedical research and biotechnological engineering.

The invention provides that IRES mediates the translation of unconventional antigens and elicits IgG antibody immune responses that are enhanced by IFN-α. Aberrantly expressed and translated antigens (26) tumor antigens were identified by SEREX (9) using sera from three PV patients who underwent IFN-α-induced remission, which identified the IRES translated unconventional antigen—MPD6. The enhancement of IRES-mediated translation of MPD6 by IFN-α is a novel mechanism of IFN-α enhanced anti-tumor immune responses.

The invention provides an isolated nucleic acid sequence selected from the group consisting of SEQ ID NO: 1, fragments thereof, variants thereof, and muteins thereof. The invention provides an isolated nucleic acid sequence encoding a polypeptide selected from the group consisting of SEQ ID NO: 2, fragments thereof, muteins thereof, and variants thereof.

The invention provides a nucleic acid comprising a reporter gene operatively linked to an MPD6-IRES region wherein the MPD6-IRES region is responsive to IFN-α. The invention further provides the nucleic acid, further comprising a nucleic acid sequence selected from the group consisting of SEQ ID NO: 1, fragments thereof, variants thereof, and muteins thereof, and, wherein the reporter gene is a luciferase gene. The invention further provides the nucleic acid, further comprising a nucleic acid sequence encoding a polypeptide selected from the group consisting of SEQ ID NO: 2, fragments thereof, muteins thereof, and variants thereof, wherein the MPD6-IRES region is responsive to IFN-α.

The invention provides a bicistronic reporter vector comprising a first reporter gene; an MPD6-IRES region; a second reporter gene; and wherein the MPD6-IRES region is responsive to IFN-α. The invention provides a host cell comprising the nucleic acid, wherein the MPD6-IRES region is responsive to IFN-α and further wherein the host cell is a member selected from the group consisting of eukaryotic cells and prokaryotic cells, and further, wherein the MPD6-IRES region is responsive to IFN-α.

The invention provides a substantially purified polypeptide selected from the group consisting of SEQ ID NO: 2, fragments thereof, muteins thereof, and variants thereof.

The invention provides a vaccine for the protection of humans against cancer, comprising: a recombinant vector virus that expresses in vivo a heterologous nucleic acid sequence selected from the group consisting of: SEQ ID NO: 1, a nucleic acid sequence encoding SEQ ID NO: 2, fragments thereof, muteins thereof, and variants thereof, together with a pharmaceutically acceptable carrier. The invention provides a vaccine composition comprising an immunogenic peptide selected from the group consisting of SEQ ID NO: 2, fragments thereof, muteins thereof, and variants thereof. The invention provides an immunogenic peptide selected from the group consisting of SEQ ID NO: 2, fragments thereof, muteins thereof, and variants thereof.

The invention provides an isolated nucleic acid encoding an immunogenic peptide selected from the group consisting of SEQ ID NO: 2, fragments thereof, muteins thereof, and variants thereof.

The invention provides an isolated antibody, wherein said antibody selectively binds a) an MPD6 polypeptide with an amino acid sequence of SEQ ID NO: 2; b) an MPD6 polypeptide that is encoded by a nucleic acid molecule that hybridizes to the nucleic acid sequence of SEQ ID NO: 1 under stringent conditions, comprising 50% formamide, 0.1% bovine serum albumin, 0.1% Ficoll, 0.1% polyvinylpyrrolidone, 50 mM sodium phosphate (pH 6.5), 750 mM NaCl, and 75 mM sodium citrate at 42° C., with washes at 42° C. in 0.2×SSC and 0.1% SDS; c) a fragment of said antibody, wherein said antibody and antibody fragment selectively bind to said MPD6 polypeptide. The invention further provides the antibody, wherein the antibody is of polyclonal or monoclonal origin.

The invention provides a method of eliciting or enhancing an immune response to a human self tumor antigen such as MPD6 (SEQ ID NO: 18), comprising immunizing a human being with an unconventional antigen that is homologous to foreign proteins or foreign peptides but normally not expressed unless stimulated by interferons or cytokines.

The invention provides a method of treating or preventing a disorder selected from the group consisting of viral infections, inflammation, autoimmune disease, and cancer comprising administering to said subject a therapeutically effective amount of the vaccine composition according to claim 12.

The invention provides a method of identifying a potential therapeutic agent for the treatment of a disorder selected from the group consisting of viral infections, inflammation, autoimmune disease, and cancer which inhibits IFN-α induced expression of MPD6 comprising the steps of: (a) providing a reporter vector comprising a reporter gene and an MPD6-IRES region, wherein the MPD6-IRES region is responsive to IFN-αc; (b) providing a test agent; (c) providing IFN-α; (d) combining the reporter vector, the test agent, and IFN-α; (e) measuring reporter gene activity in the presence of test agent; (f) measuring reporter gene activity in a control sample; and (g) comparing reporter gene activity in the control sample compared to the test sample, to identify a compound which modulates a disorder selected from the group consisting of viral infections, inflammation, autoimmune disease, and cancer, further wherein the reporter vector comprising a reporter gene and the MPD6-IRES region responsive to IFN-☐ is in a stably transfected cell line, wherein the cell is a member selected from the group consisting of eukaryotic cells, and prokaryotic cells. The invention provides the method, wherein the reporter gene is a luciferase gene.

The invention provides a method of treating a disorder selected from the group consisting of viral infections, inflammation, autoimmune disease, and cancer in a patient in need thereof by administration of an effective amount of a compound which modulates the activity of a member of the group selected from MPD6, the MPD6-IRES region activity, and combinations thereof.

The invention provides a kit comprising an immunogenic peptide comprising an immunogenic peptide selected from the group consisting of SEQ ID NO: 2, fragments thereof, muteins thereof, and variants thereof.

The invention provides a method of identifying a potential therapeutic agent which inhibits a disorder selected from the group consisting of viral infections, inflammation, autoimmune disease, and cancer comprising the steps of: (a) providing a cell comprising a reporter gene operatively linked to an MPD6-IRES region; (b) contacting the cell with a test agent in the presence of IFN-α, wherein a decrement in the expression of the reporter gene in the presence of IFN-α and the test agent, as compared to the expression of the reporter gene in the presence of IFN-α and the absence of the test agent, indicates that the test agent is a potential cancer therapeutic.

The invention provides a method of identifying a potential therapeutic agent which a disorder selected from the group consisting of viral infections, inflammation, autoimmune disease, and cancer comprising the steps of: (a) providing a cell comprising a reporter gene operatively linked to an MPD6-IRES region, and the reporter gene; (b) contacting said cell with a test agent under conditions wherein said cells express the reporter gene, wherein a decrement in the expression of the reporter gene as compared to a control indicates that the test agent is a potential therapeutic for a disorder selected from the group consisting of viral infections, inflammation, autoimmune disease, and cancer, and further, wherein the cell is a member selected from the group consisting of eukaryotic cells, and prokaryotic cells, and further wherein the reporter gene is a luciferase gene.

The invention provides a diagnostic kit for the detection of MPD6 antigen comprising a container comprising at least one antibody wherein the at the least one antibody specifically binds to an epitope of MPD6, further comprising a solid support, wherein the solid support is selected from the group consisting of wells of reaction trays, test tubes, polystyrene beads, strips, membranes and microparticles. The invention further provides the diagnostic kit, further comprising a label, wherein the label is selected from the group consisting of enzymes, radioisotopes, fluorescent compounds and chemiluminescent compounds, and further wherein the enzymatic label is horseradish peroxidase. The invention further provides the diagnostic kit further comprising a hapten and labeled anti-hapten system wherein the hapten is conjugated to a labeled murine monoclonal antibody.

The invention provides a method for detecting the presence of MPD6 peptide in a biological sample comprising a) contacting a biological sample with an anti-MPD6 antibody to form a MPD6-antibody complex; b) contacting the MPD6-antibody complex with a detection antibody so that the detection antibody binds to the soluble MPD6-antibody complex; and c) detecting the presence of the detection antibody that bound to the MPD6-antibody complex, thereby detecting the presence of MPD6 peptide in the sample, and further wherein the biological sample is a member selected from the group consisting of whole blood, serum, plasma, cerebrospinal fluid, saliva, urine, spinal fluid, synovial fluid, amniotic fluid and cranial fluid, and lymphocyte or cell culture supernatants.

The invention provides a method for monitoring the course of disease in a patient which comprises quantitatively determining in a first cell sample from the subject the presence of MPD6 peptide and comparing the amount so determined with the amount present in a second sample from the subject, such samples being taken at different points in time, a difference in the amounts determined being indicative of the course of disease.

The invention provides a method for monitoring the course of disease in an cancer patient subject which comprises: obtaining a first sample from the subject; determining from the first sample at least one measure of a MPD6 peptide; at a different time, obtaining a second sample from the subject; determining from the second sample at least one measure of a MPD6 peptide; wherein a difference in the measured MPD6 peptide determined from the first sample and the second sample being indicative of the course of disease.

The invention provides a method of diagnosing a disease condition related to a disorder selected from the group consisting of viral infections, inflammation, autoimmune disease, and cancer in a patient comprising: obtaining a blood sample from the patient; determining from the sample at least one measure of a MPD6 peptide; presenting such measure; and applying the measure of the MPD6 peptide selectively as a diagnostic evaluation of a disease condition related to a disorder selected from the group consisting of viral infections, inflammation, autoimmune disease, and cancer.

BRIEF DESCRIPTION OF SEVERAL VIEWS OF THE DRAWINGS

The invention will be described in conjunction with the following drawings in which like reference numerals designate like elements and wherein.

DETAILED DESCRIPTION OF THE INVENTION

Figure 1A:
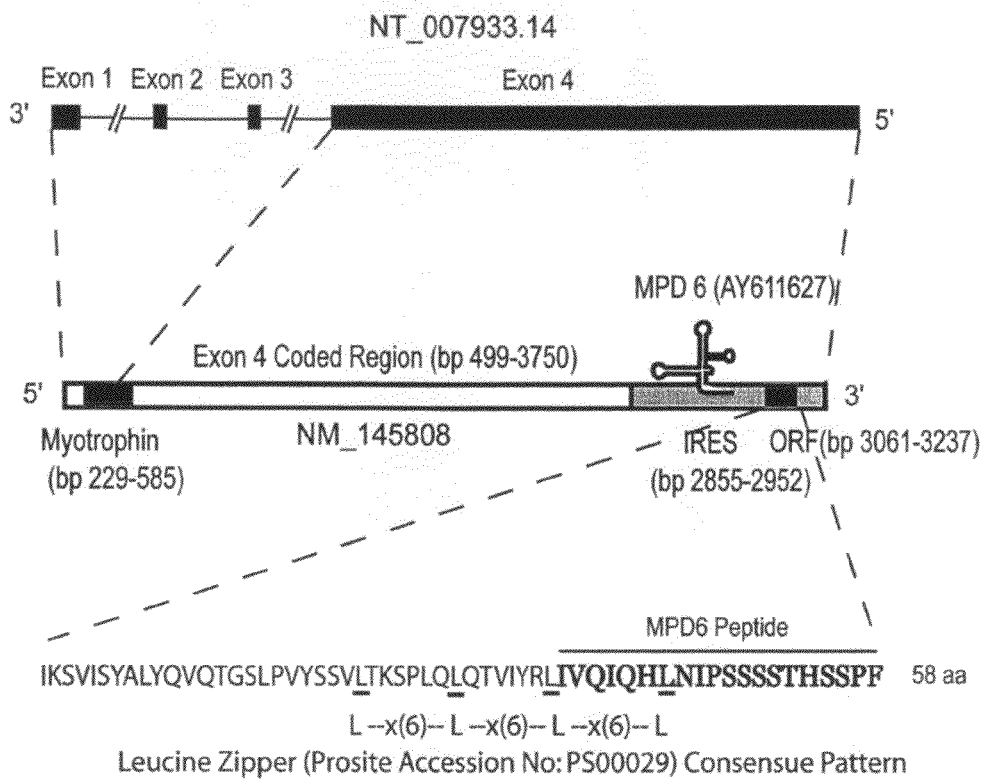
FIG. 1. Molecular Features of MPD6. A. Schematic representation of the location of unconventional antigen MPD6 gene in the 3' untranslated region (3'UTR) of myotrophin mRNA (GenBank accession number: NM_145808) as well as the genomic structure of the myotrophin-MPD6 gene locus (GenBank accession number: NT_007933.14). The MPD6 open reading frame (ORF) (GenBank accession number: AY611627 (SEQ ID NO: 1)) is located in the region by 3061-3237 in the 3'UTR of myotrophin, while the primary ORF myotrophin is located in the region by 229-585. An internal ribosome entry site (IRES) is also located in the region of the 3'UTR of myotrophin, by 2855-2952 upstream of MPD6 ORF (SEQ ID NO: 18). B. Feature of MPD6 protein sequence. The MPD6 ORF encodes a 58 amino acid protein. (SEQ ID NO: 19). The start codon is an unconventional start codon AUU (isoleucine), rather than the conventional start codon AUG (methinione). Hydrophilicity plot analysis using by Kyte-Dolittle method indicated that MPD6 has a C-terminal hydrophilic region, which corresponds to the region achieving the higher Jameson-Wolf antigenic index. The Jameson-Wolf antigenic index in the MPD6 C-terminal region is higher than that of previously characterized antibodies recognized epitope threshold (the mean-$2.\text{times}.\text{SD}=1.56$). MPD6 peptide used in the ELISA was synthesized according to the MPD6 sequence from aa 39 to aa 58. C. Higher expression of Myotrophin-MPD transcripts in some tumor cells detected by Northern blots. In the upper panel, the lanes N1 to N10 indicate various normal tissues in the order of brain (N1), liver (N2), placenta (N3), small intestine (N4), colon (N5), thymus (N6), spleen (N7), prostate (N8), testis (N9), and ovary (N10), respectively. In the middle panel, the lanes T1 to T 10 indicate various tumor cells in the order of acute T cell leukemia (Jurkat cells) (T1), Burkitt's lymphoma (CA46) (T2), breast cancer (MDA-MD-453) (T3), Burkitt's lymphoma (Namalwa) (T4), epidermial carcinoma (A-431) (T5), uterine carcinoma (MES-SA) (T6), Burkitt's lymphoma (Raji) (T7), osterosarcoma (MG-63) (T8), histiocytic lymphoma (U-937) (T9), and cervical adenocarcinoma (Hela S3) (T10), respectively. The hybridization analyses of the normal tissue and tumor cell expression (Clontech) with 32P-labelled specific probes, as indicated, were performed, respectively. The transcript sizes are indicated with kilobases (kb). The ratio of the hybridization signal density of MPD6 transcript over the hybridization signal density of .beta.-actin in the same sample was calculated as relative densitometric unit as presented in the lower panels. D. The IgG antibody responses to the C-terminal antigenic epitope (from the aa 39 to the aa 58) of MPD6 detected by peptide ELISA. The experiments were repeated three times, the representative results were shown. The mean plus three times standard deviation (SD) of the OD405 ratios of the peptide over the coating control from 24 healthy donors were calculated as the upper limit of the normal range of antibody responses to MPD6 peptide (the mean+2SD=1.26). The detection rates of the IgG antibody responses to MPD6 peptide in the group of CML patients treating with IFN-.alpha. are statistically higher than that of CML patients treating with other therapies (the Chi-Square Goodness-of-Fit Test; $p<0.05$, marked with *).

Identification of a Novel MPD-Associated SEREX Antigen, MPD6

The human testis expression cDNA library was screened by SEREX using diluted sera collected from the patients with PV who responded to IFN-α therapy (2). Testis is an immune privileged site where self-antigens are not presented to host immune system (33, 34). As reported by studies in other tumors (26, 35, 36), screening a testis expression cDNA library using SEREX with sera from various tumor patients has proved to be a useful approach to identifying the tumor-associated antigens that are aberrantly expressed in tumors but not normal tissues. PV patients were chosen for cDNA library screening based on two criteria: 1. The patients had undergone remission in response to IFN-α treatment as judged by conversion from monoclonal to polyclonal hematopoiesis determined by X-chromosome transcriptional polymorphism analyses (2); and 2. Normalization of hemoglobin concentration and platelet count on IFN-α therapy (2, 3). Two of the three PV females with favorable response to IFN-α treatment were previously reported (2). Initial screening of $1\times10^6$ recombinant phage clones was followed by several rounds of the purification of positive phage plaques and further confirmation on their antigen specificities. A unique cDNA clone was identified.

Figure 1B:
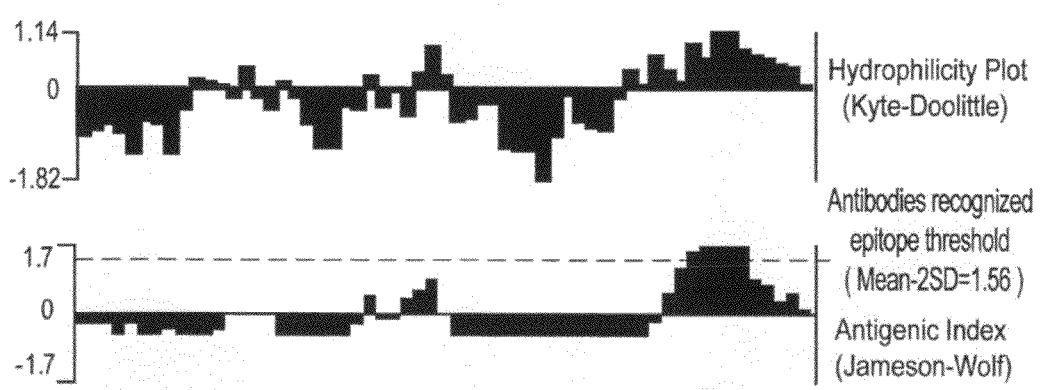

The isolated clone (710 by insert) was identical to myotrophin mRNA (FIG. 1A). Myotrophin interacts with rel/NF-kB (37, 38) and converts NF-kB p50-p65 heterodimers to homodimers (39). In contrast to DC6 encoded by the cDNA sense strand of tumor antigen CML66 that we previously reported (20), the coding sequence of the isolated clone was located in the mRNA-sense strand of myotrophin mRNA, however, the coding sequence was in the 3'UTR (bp 3061-3237) of myotrophin mRNA (37) (FIG. 1A). Sequence analysis revealed an ORF that encoded 58 amino acids located in frame 1 (the same as that of myotrophin) (FIG. 1B). Since the size of the predicted protein encoded by this ORF was 6.4 kD, we referred it to as MPD6. MPD6 could not result from a mechanism of termination codon readthrough (40) since there were 40 in-frame stop codons between the myotrophin ORF and that of MPD6 (not shown). The myotrophin-MPD6 gene locus spans 50.7 kb in human chromosome 7q33 with 4 exons. Exon 4 encodes an mRNA from by 499 to by 3750, which covers the C-terminal 29 amino acids of myotrophin and a 3'UTR that also includes the MPD6 reading frame (FIG. 1A). Thus, MPD6 and myotrophin share the same mRNA transcript that is independent of alternative splicing (FIG. 1A). Therefore, MPD6 can not be generated by the following two mechanisms: (1) encoding by a separated exon potentially transcribed by a cryptic promoter as showed for transcription of self-tumor antigen CML66L isoform, CML66S (20); and (2) integration into the C-terminus of myotrophin by exon skipping mechanism (41).

The MPD6 reading frame had neither a canonical start codon (AUG) nor an optimal Kozak consensus sequence (A/GNNAUGG) (SEQ ID NO: 20; SEQ ID NO: 21) (42). However, this sequence started with the unconventional start codon AUU encoding isoleucine (17, 18), one of the start codons that was previously demonstrated to initiate cryptic antigen peptide translation (19, 43). Moreover, this reading frame matched one (the slip frame) of the three forward fusion frames of the library vector pTriplEx, suggesting that MPD6 sequence fused in the library vector was recognized by antibodies in the sera of patients during SEREX screening. The predicted MPD6 amino acid sequence showed no significant homologies to any known proteins in the NCBI-GenBank databases and the SEREX database, indicating that it is a novel protein. The following features of MPD6 demonstrate that it is a human protein-encoding sequence: (1) the frequencies of amino acid codon usage including those amino acid residues with multiple codons (44) were identical to those used in human proteins; (2) the analysis of protein domains and motifs on the PROSITE database demonstrated that two overlapped regions of MPD6, including the first one from aa 17 to aa 38, and the second one from aa 24 to aa 45, were identical to the leucine zipper pattern (Leu-x(6)-Leu-x(6)-Leu-x(6)-Leu) (the PROSITE ID#: PS00029) (FIG. 1B), which mediates the dimerization of transcription factors and other regulatory proteins (45). The two overlapping leucine zippers in MPD6 could not have been generated randomly, since the chance of occurrence of leucine at any given position in proteins is 0.09 (44) and the random chance of the frequency for MPD6 to have the simultaneous occurrence of leucine at these five defined positions is extremely low ($0.09^5 = 5.9 \times 10-6$). These characteristics indicate that the non-random leucine zipper patterns may fulfill a specific cellular function. Thus, MPD6 has the characteristics of short protein-encoding ORFs as previously reported (46).

*Homo sapiens* myeloproliferative disease-associated SEREX antigen mRNA was deposited with GenBank, accession number AY611627 (SEQ ID NO: 1).

The novel antigen MPD6 was identified using sera from female patients; however, myotrophin-MPD6 gene loci is located on human autosomal chromosomes 7q33 (80) rather than on the Y chromosome, indicating that anti-tumor immune responses enhanced by IFN-α therapy in CML but not PV are at least partially mediated by novel self-tumor antigens, rather than Y chromosome-encoded male-specific antigens (80). Correlation of antigen-specific IgG immune responses with the remission in PV and CML patients (3, 81) indicated that immune responses mediated by both unconventional and conventional antigens may contribute to the MPD remission.

Upregulated Expression of Myotrophin-MPD6 Transcripts in Some Tumor Cells

Detection of IgG antibodies to MPD6 in patients with tumors indicates that expression of myotrophin-MPD6 transcripts is upregulated in some tumors. Since MPD6 is always located in the same 3.77 kb transcripts with myotrophin ORF, therefore, the 3.77 kb myotrophin-MPD6 mRNAs detected by Northern blots confirm the authenticity of MPD6. The Northern blots examining the expression of MPD6 transcripts in 10 normal tissues are depicted in the upper panel of FIG. 1C. To avoid possible variation in sample preparation and loading, the ratio of the density of MPD6 transcript over the density of β-actin in the same sample was calculated as relative densitometric unit (32). Low levels of expression (<75 relative densitometric units) were found in brain (N1), spleen (N7), testis (N9), and ovary (N10). In contrast, MPD6 expression was significantly upregulated (>85 relative densitometric units) in a variety of tumor cells (the lower panel of FIG. 1C), including Burkitt's lymphoma (Namalwa) (T4), epidermal carcinoma (A-431) (T5), uterine carcinoma (MES-SA) (T6), Burkitt's lymphoma (Raji) (T7), histiocytic lymphoma (U-937) (T9), and cervical adenocarcinoma (Hela S3) (T10).

Detection of MPD6-Specific IgG Antibodies in Patients with PV, CML and Prostate Cancer.

As shown in the lower panels of FIG. 1B, MPD6 has one hydrophilic region and also achieved high antigenic index scores (47), indicating that this region has potential to be a binding epitope for antibody interactions. We previously showed that the mean±2 times standard deviation (SD) of the Jameson-Wolf antigenic scores of 43 experimentally verified, antibody-recognized antigenic epitopes of self-antigens (48) was in the range of 1.56 to 4.36 (21). These analyses indicate that one antigenic epitope in MPD6 with the Jameson-Wolf antigen index scores of 1.7 had good potential (p<0.05) in the elicitation of specific antibody responses. To verify whether MPD6 antigen epitope is immunogenic in vivo, a MPD6 peptide was synthesized using the amino acid sequence of the second antigen epitope of MPD6 from aa 39 to aa 58. The ELISA using the MPD6 peptide showed that the MPD6 epitope-specific IgG antibody responses could be detected in 7.7% and 5.7% of PV patients receiving either IFN-α or other therapies, respectively (FIG. 1D). In addition, MPD6-specific IgG antibody responses could be detected in 15.6% and 5.0% of CML patients receiving either IFN-α or other therapies, respectively. Furthermore, anti-MPD6 IgG antibodies were also found in 23.7% of patients with prostate cancer. These results indicate that MPD6 was not only immunogenic in patients with PV, but also broadly immunogenic in patients with other tumors. Previous studies showed that the incidence of IgG antibody immune responses to the aberrantly expressed self-tumor antigens ranges between 5% and 50%, depending on the tumor type and the respective antigen (49). Therefore, the antibody responses to MPD6 in patients with tumors were in the range similar to that of other self-tumor antigens. It is noteworthy that the detection rates of anti-MPD6 IgG antibodies were much higher in CML patients receiving IFN-α than in CML patients receiving other therapies (p<0.05). This indicates that IFN-α therapy will enhance the anti-MPD6 immune responses either by upregulation of MPD6 expression or by enhancement of immune responses to MPD6 antigen. Enhancement of immune responses to MPD6 was not observed in PV patients receiving IFN-α in comparison to that in PV patients receiving other therapies, which indicates a disease-specific effect of IFN-α. It is well accepted that Western blots are a good indicator of specific antigen-antibody interaction. Based on this principle, detection of specific antibodies to the C-terminal peptide of MPD6 in patients using SEREX indicates that: (1) MPD6 was expressed in a subset of patients with tumors; and (2) the full-length MPD6 will be expressed since the C-terminus of MPD6 is the last part of MPD6 sequence to be translated in protein synthesis.

Figure 2A:
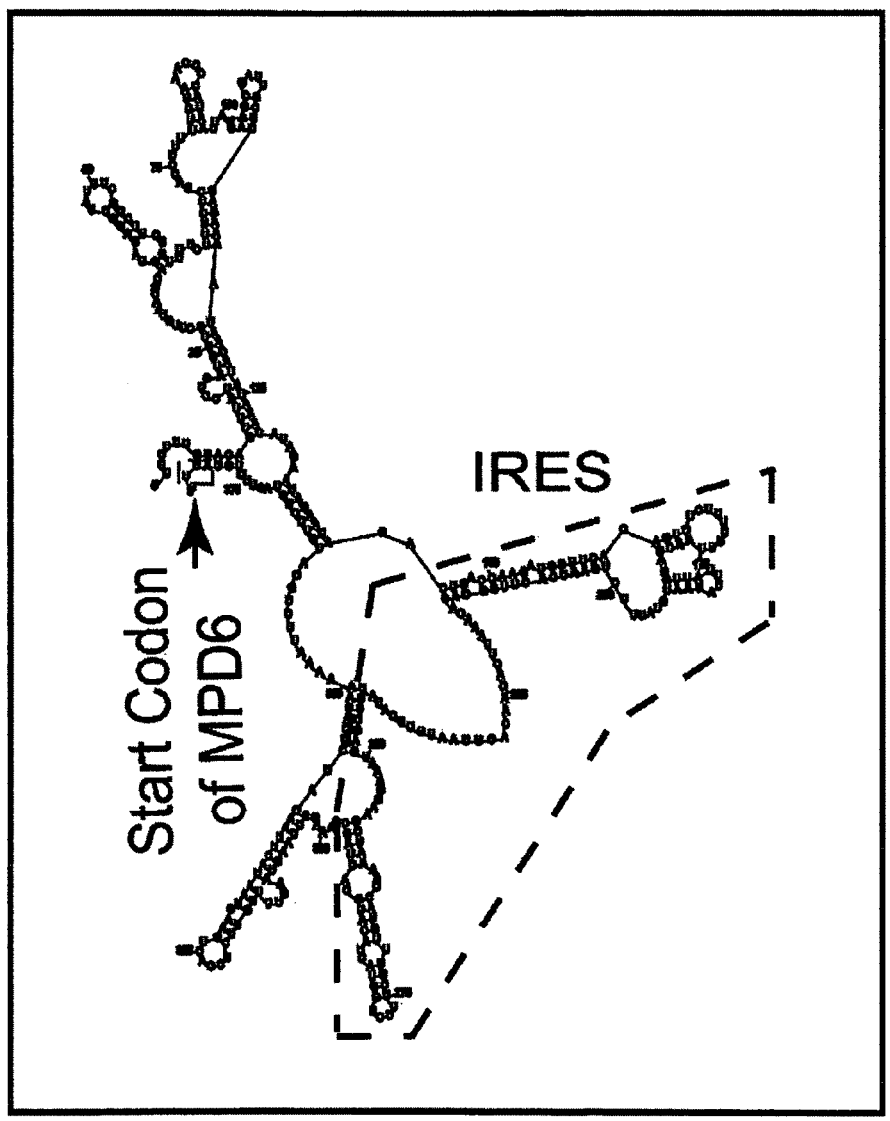
FIG. 2. The predicted stem-loop structure in MPD6-IRES. The cis-acting regulatory elements in 3' untranslated region (3'UTR) were analyzed using the IRES website at and the UTR website at with generous support by Dr. Sabino Liuni at the Bioinformatics and Genomic Group in Italy. The secondary structures of MPD6-IRES (A and D), EMCV-IRES (B and E), and XIAP-IRES (C and F) were predicted by using two web-based algorithms MFOLD-Zuker (A, B, and C), and the RNAfold (D, E, and F). The free energy of the secondary structure of these IRES regions were also calculated with both algorithms. The start codon and IRES region of MPD6 are indicated.
Figure 2B:
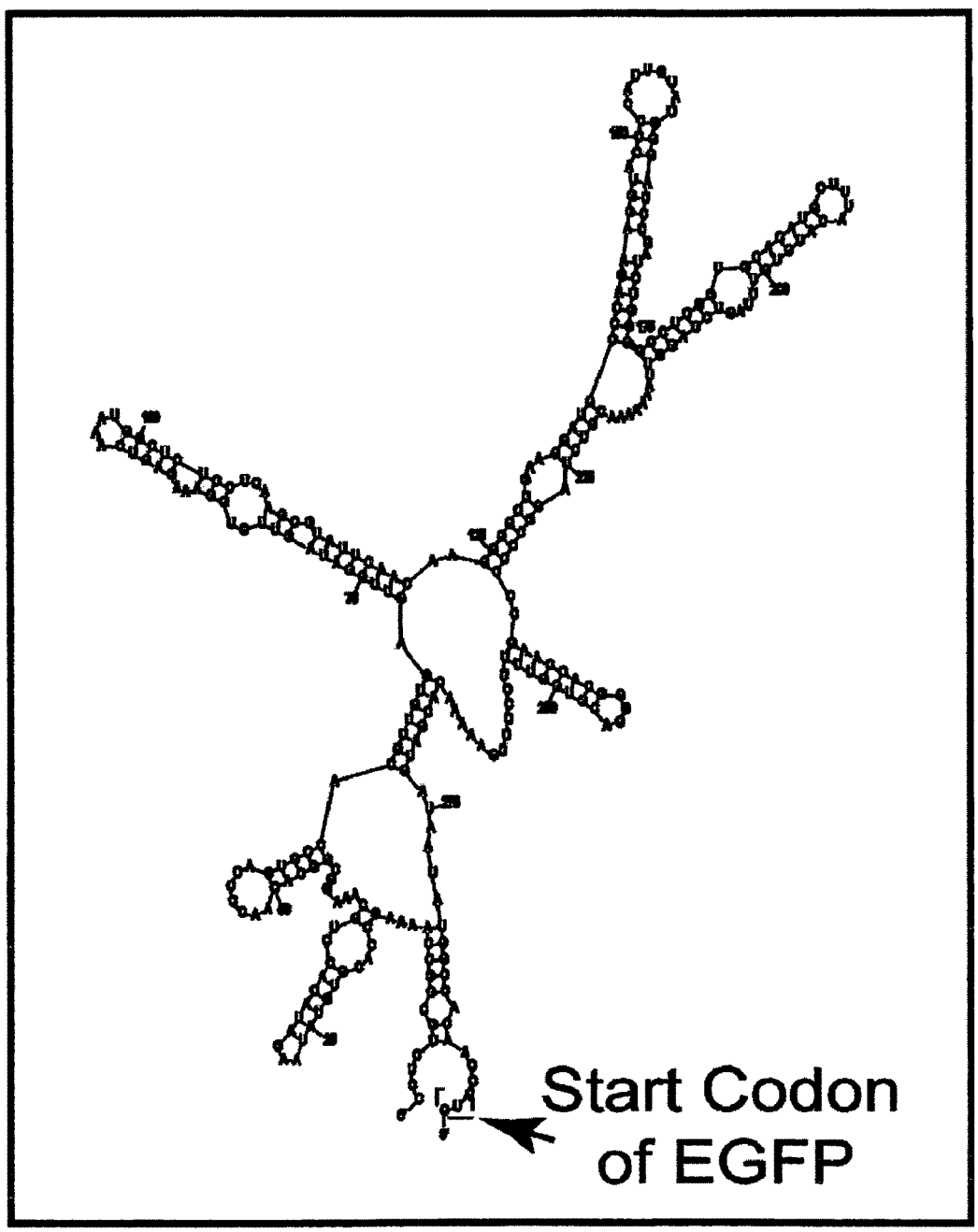
Figure 2C:
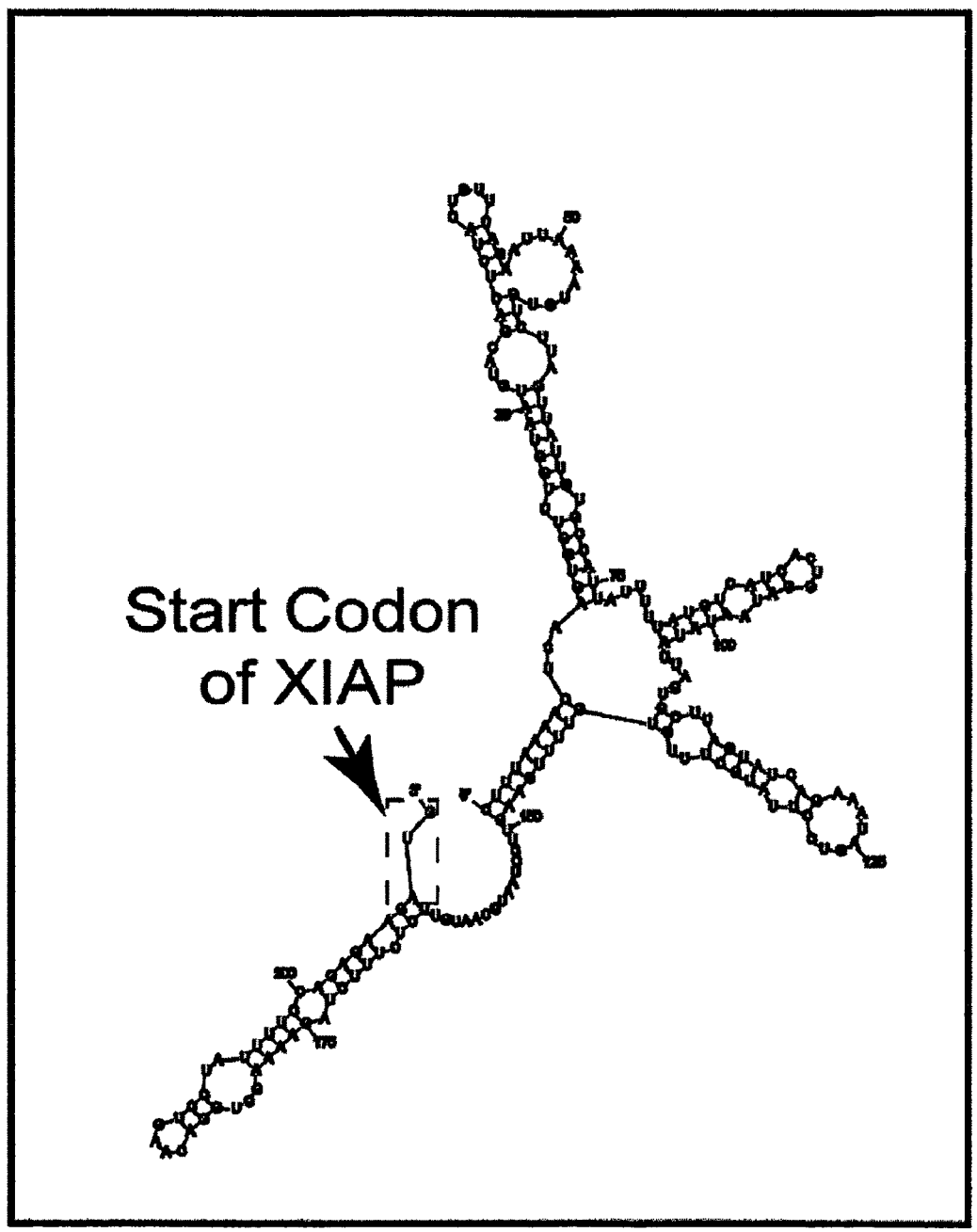
Figure 2D:
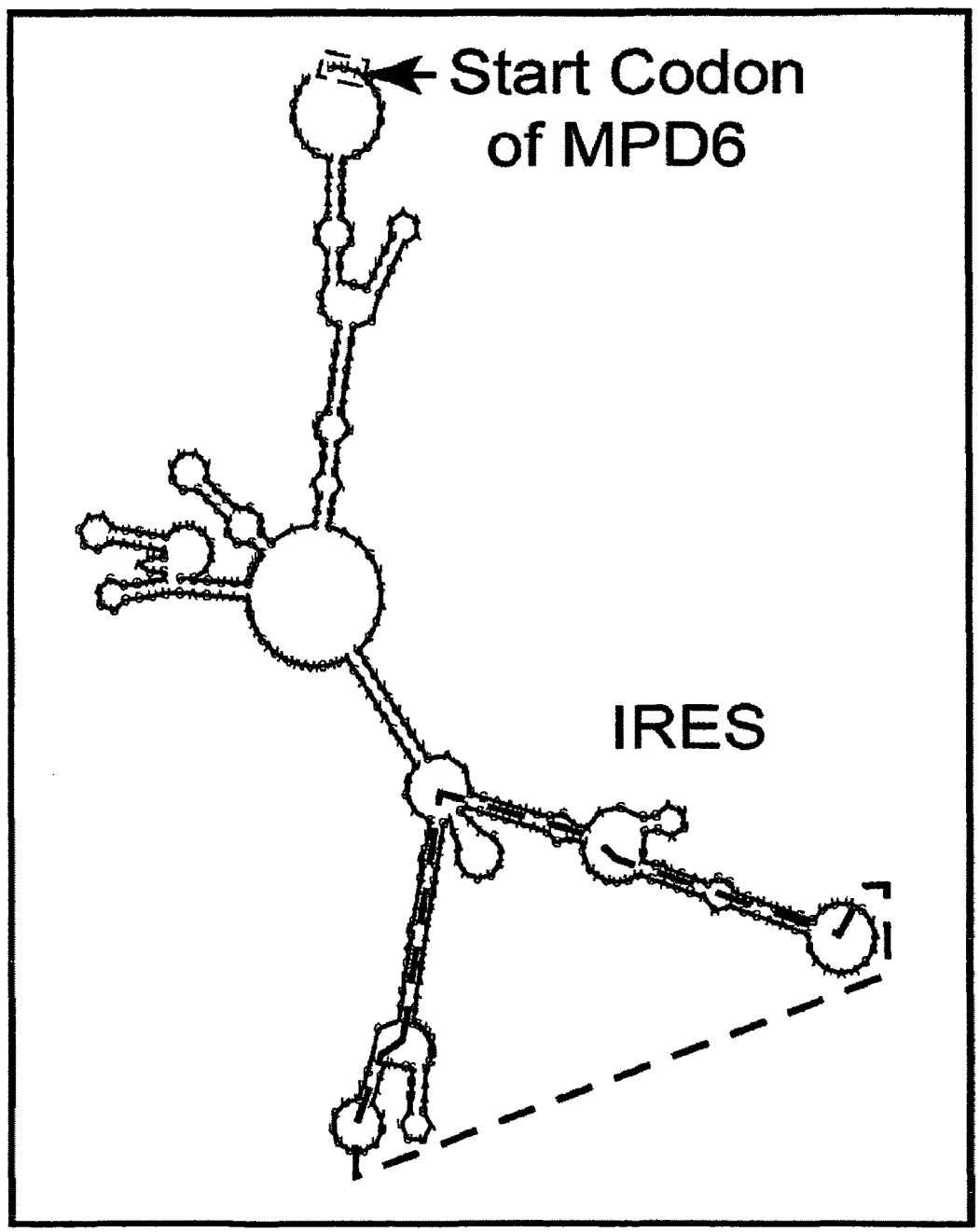

The Translation of MPD6 is Mediated by an Internal Ribosome Entry Site (IRES), which is Enhanced by IFN-α Stimulation The mechanism of translation of the cryptic ORF located in the 3'UTR of myotrophin into a protein antigen was determined. Potential IRESs located in the upstream of MPD6 promoted the translation of MPD6 were examined and the analysis of the UTR database (27) showed an IRES-containing region located upstream of MPD6, as shown in FIGS. 1A, 2A, and 2D. Since some cellular IRESs may contain a common Y-type stem-loop structural motif (50), the sequences upstream of MPD6 were searched for stable stem-loop structures by applying two prediction algorithms for RNA secondary structure, MFOLD (28) and RNAfold (29) for the prediction accuracy higher than that using one algorithm. As shown in FIG. 2, the encephalomyocarditis virus (EMCV) IRES region from the widely-used bicistronic expression vector IRES2-EGFP had a stable stem-loop structure with a low free energy; i.e. −112.9 kcal/mol (the MFOLD algorithm, FIG.

Figure 2E:
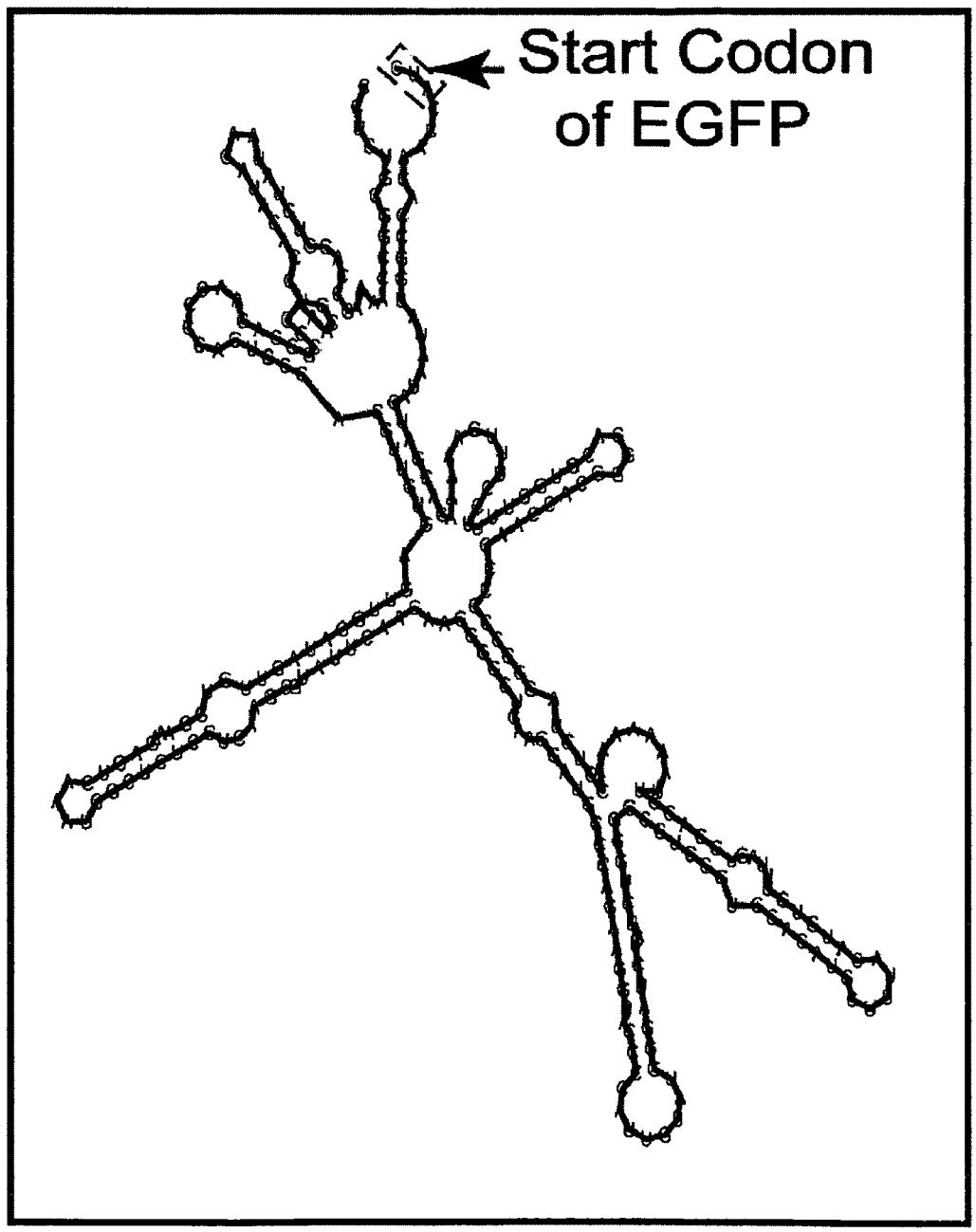
Figure 2F:
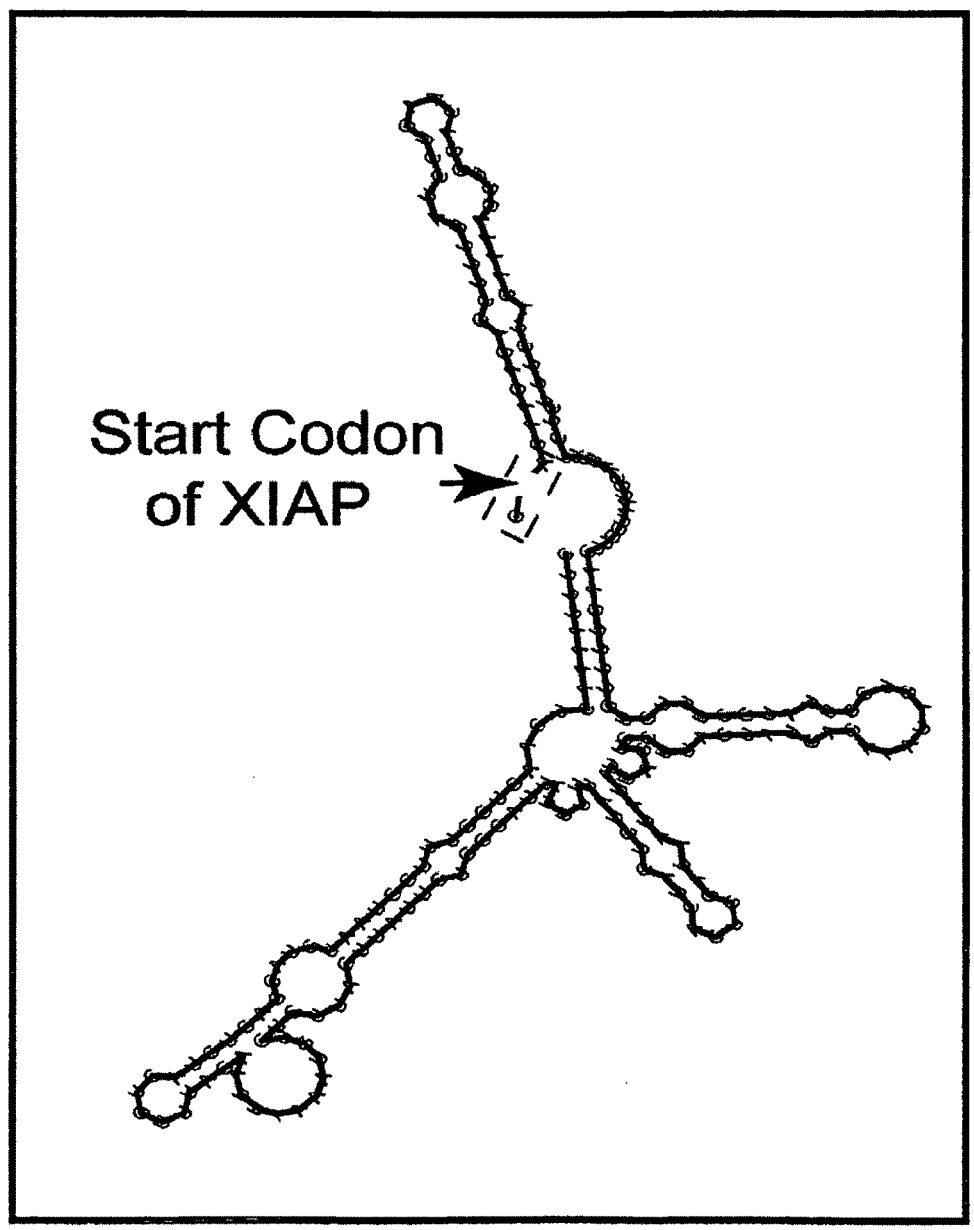

2B), or −123.34 kcal/mol (RNAfold algorithm, FIG. 2E). We also show that the IRES-containing region located upstream of MPD6 has a stable stem loop structure with the free energy of either −77.2 kcal/mol calculated by the MFOLD algorithm (FIG. 2A) or −90.39 kcal/mol calculated by the RNAfold algorithm (FIG. 2D). Experimentally verified XIAP IRES (51) (FIG. 2C and FIG. 2F) had a free energy higher than that of the MPD6 IRES region (FIGS. 2A and D) by using the same MFOLD and RNAfold algorithms (28), which indicate that MPD6 IRES may have a stem loop structure more stable than that of the experimentally verified XIAP IRES. Since a lower free energy of the RNA secondary structure is associated with higher stability of the structure (28, 29), these analyses indicate that the IRES-containing region located upstream of MPD6 is remarkably stable for fulfilling IRES function (28, 29).

Figure 3A:
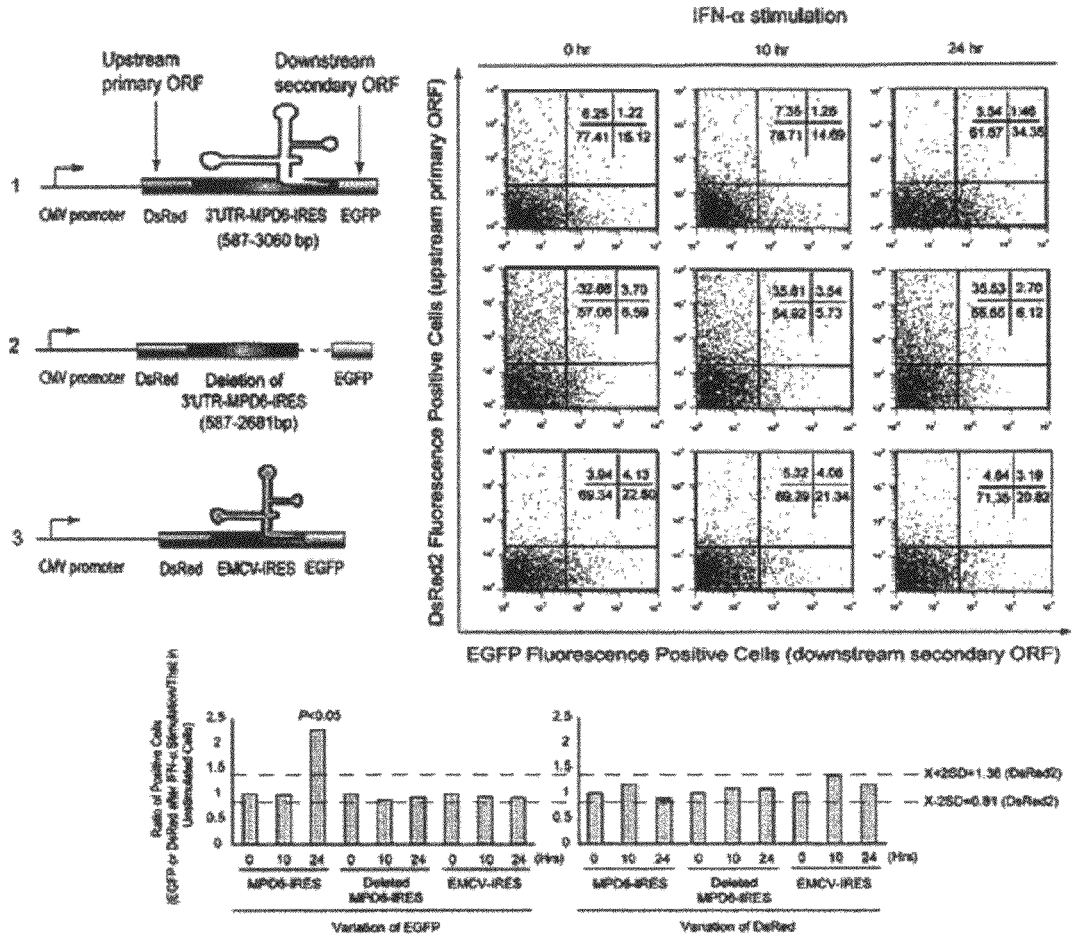
FIG. 3. Upregulated translation of EGFP directed by MPD6-IRES in response to Interferon-α (IFN-α) stimulation. A. Following bicistronic vectors with DsRed as the upstream primary open reading frame (ORF) and with EGFP as the downstream secondary ORF were constructed (upper left panel), including (1) a complete sequence (myotrophin 3'UTR plus MPD6-IRES) between myotrophin ORF and MPD6 ORF was placed between DsRed ORF and EGFP ORF; (2) a deletion mutant with the 5' portion of the myotrophin 3'UTR but having no MPD6-IRES region in between DsRed ORF and EGFP ORF; and (3) a bicistronic vector control with EMCV-IRES as an documented IRES positive control. The non-transfected cells were used as a negative control for DsRed and EGFP expression (not shown). In the upper right panels, the bivariate plots show the DsRed fluorescence positive cells (ordinate) and the EGFP fluorescence positive cells (abscissa), and percentages of cells in each quadrant in the K562 cells stably-transfected with each bicistronic reporter construct, and stimulated with IFN-α for 0, 10, and 24 hours. The experiments were repeated three times, the representative results were shown. In the lower right panel, the confidential intervals (the mean±2SD=0.81 to 1.36, shown in the dash lines) of the ratio of the percentage of DsRed positive cells after IFN-α stimulation over that before IFN-α stimulation were generated. Similarly, in the lower left panel, the ratio of the percentage of EGFP positive cells after IFN-α stimulation over that before IFN-α stimulation were calculated. The ratio of the percentage of EGFP positive cells in MPD6-IRES transfected group 24 hrs after IFN-α stimulation over that before IFN-α stimulation was 2.3, which was significantly higher than the upper limit (1.36) of the DsRed confidential intervals (p<0.05). B. The expression of eIF-2 α and phosphorylated eIF-2 α in K562 myeloid leukemia cells stimulated with IFN-α detected by specific antibodies. The upregulation of the expression of eIF-2 α and phosphorylated eIF-2 α in responses to IFN-α stimulation in myeloid leukemia K562 cells was measured by Western blots with specific antibodies to eIF-2 α and phosphorylated elf-2 α, respectively, at the time points as indicated. The Western blot with antibodies to β-actin was performed as a house keeping protein control and a no-response control for IFN-α stimulation. In the right panel, the relative densitometric units were calculated by normalizing the densities of the eIF-2 α and phosphorylated eIF-2 α with that of β-actin in the same sample. The relative densitometric units for the expression of eIF-2 α and phosphorylated eIF-2 α after IFN-α stimulation over that before IFN-α stimulation were calculated and shown as the percentages. C. The MPD6 expression in K562 myeloid leukemia cells stimulated with IFN-α detected by semi-quantitative RT-PCR. The upregulation of MPD6 transcripts in responses to IFN-α stimulation in myeloid leukemia K562 cells was measured by semi-quantitative RT-PCR at the time points as indicated (the left panel). The RT-PCR amplification of β-actin transcripts was performed as a house keeping gene control for RT-PCR and a no-response control for IFN-α stimulation. The RT-PCR amplification of ISG15 was used as a positive control for IFN-α stimulation. In the right panel, the relative densitometric units were calculated by normalizing the densities of the PCR products of MPD6 and ISG15 with that of β-actin in the same sample. The relative densitometric units for the expression of myotrophin/MPD6 and ISG15 transcripts after IFN-α stimulation over that before IFN-α stimulation were calculated and shown as the percentages. D. The proposed working model of MPD6 translation mediated by MPD6-IRES. MPD6-IRES is found to be capable in mediation of upregulated translation of MPD6 in response to IFN-α stimulation, which may result from IFN-α mediated phosphorylation of eIF-2 α.

To verify that the IRES-containing structure upstream of MPD6 has IRES function, a set of bicistronic reporter gene vectors were constructed with DsRed as the upstream primary ORF and EGFP as the downstream secondary ORF; the latter was translated under the direction of IRES (FIG. 3A). The translation of the downstream secondary ORF EGFP by measuring green fluorescence with flow cytometry, and the translation of the upstream primary ORF DsRed by measuring red fluorescence. As shown in FIG. 3A-1-0 hr, the MPD6 IRES region mediated significant translation (2.3 fold) of the downstream EGFP (15.12%) in the absence of IFN-α stimulation, in comparison to the deletion of IRES control (6.59%) (FIG. 3A-2-0 hr) and the positive control EMCV-IRES (22.60%) (FIG. 3A-3-0 hr). These results indicate that similar to EMCV-IRES, MPD6-IRES upstream MPD6 ORF has the IRES function to mediate the translation of downstream ORF.

The higher rates of anti-MPD6 IgG antibodies in patients with CML treated by IFN-α (FIG. 1E) and the IRES mediated translation of MPD6 raised a possibility that IRES-mediated MPD6 translation will be enhanced by treatment of IFN-α. K562 cells stably expressing bicistronic vectors were treated with IFN-α for 0 hours, 10 hours and 24 hours before examining the expression of DsRed and EGFP. For examination of transfection efficiency, as shown in FIG. 3A-2-0 hr (in the absence of MPD6-IRES), the protein translation of DsRed was 36.36% (DsRed single positive+DsRed-EGFP double positive=32.66%+3.70%), indicating that transfection efficiency after G418 selection was high. DsRed and EGFP double positive cells were low throughout all the experimental groups. Moreover, deletion of MPD6-IRES resulted in increased expression of DsRed from 6.25% in FIG. 3A-1-0 hr to 32.66% in FIG. 3A-2-0 hr. The interference of EGFP translation over DsRed translation is not unique to the DsRed-MPD6-IRES-EGFP transfected cells since the same effect was observed in the control DsRed-EMCV-IRES-EGFP transfected cells (FIG.-3A-3-0 hr). Relative translation interference between the two reading frames occurs, similar to that reported previously (52). Regardless of interference of EGFP translation over DsRed translation, due to the inclusion of appropriate controls, this system was used to address two issues: (a) potential translation function of MPD6-IRES; and (b) potential responses of MPD6-IRES to IFN-α stimulation. The MPD6-IRES mediated EGFP expression was significantly upregulated (2.3 folds) from 15.12% (FIG. 3A-1-0 hr) to 34.35% (FIG. 3A-1-24 hr) in comparison to the nearly unchanged percentages of the green fluorescence positive cells in the MPD6-IRES deletion control-transfected cells after IFN-treatment (6.59% in FIG. 3A-2-0 hr and 6.12% in FIG. 3A-2-24 hr). Since the deletion of MPD6-IRES vector still remained a large portion of myotrophin 3'UTR (FIG. 3A-2), the deletion of MPD6-IRES completely abolished the response to IFN-α stimulation, indicating that the response of the MPD6-IRES-transfected cells with upregulated EGFP expression to IFN-α treatment was MPD6-IRES region-dependent. In contrast, EMCV IRES-mediated EGFP expression remained stable from 0 hour (22.60% in FIG. 3A-3-0 hr) to 24 hours (20.82% in FIG. 3A-3-24 hr) after IFN-α stimulation, indicating that the response of IRES-mediated protein translation to IFN-α stimulation was MPD6-IRES specific. Of note, EGFP downstream of MPD6-IRES was the secondary ORF in the bicistronic mRNA transcript that did not contain any introns and splicing signals (53). Therefore, the EGFP translation (FIG. 3A-1) could not be mediated by m7G cap-dependent mechanism or regulated by RNA alternative splicing. In addition, we considered the possibility that the response of MPD6-IRES mediated EGFP translation to IFN-α stimulation might result from the response of the CMV promoter to IFN-α stimulation. Thus, the translation of the upstream primary ORF DsRed was measured. As shown in FIGS. 3A-2-0 hr, 3A-2-10 hr, 3A-2-24 hr, the protein translation of DsRed was in the range of 32.66% to 35.53%, indicating that both CMV promoter activities and the m7G cap dependent translation of the upstream primary ORF were not affected by IFN-α stimulation, which served as the no response controls. As shown in the lower right panel of FIG. 3A, the confidential intervals (the mean±2SD=0.81 to 1.36) of the ratio of the percentage of DsRed positive cells after IFN-α stimulation over that before IFN-α stimulation were generated as the confidential intervals for no response variations. Similar to reported above, the ratio of the percentage of EGFP positive cells in MPD6-IRES transfected group 24 hrs after IFN-α stimulation over that before IFN-α stimulation was 2.3, which was significantly higher than the upper limit (1.36) of the DsRed confidential intervals ($p<0.05$) (the lower left panel of FIG. 3A). It was of concern that enhanced expression of MPD6-IRES mediated EGFP expression by IFN-α stimulation may have resulted from decreased degradation of EGFP. However, exchange of DsRed in the secondary ORF position and placed EGFP in the primary ORF position, the results stayed the same as shown in FIG. 3A-1 (not shown). These results show that MPD6-IRES has IRES function, which is enhanced by IFN-α stimulation.

Figure 3B:
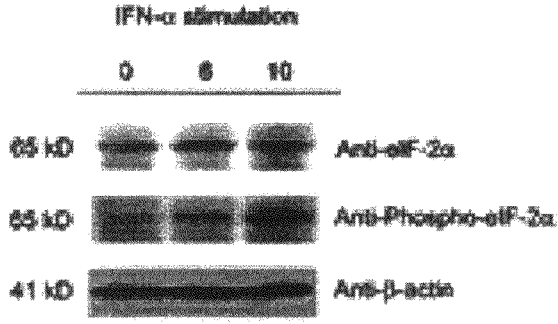
Figure 3B:
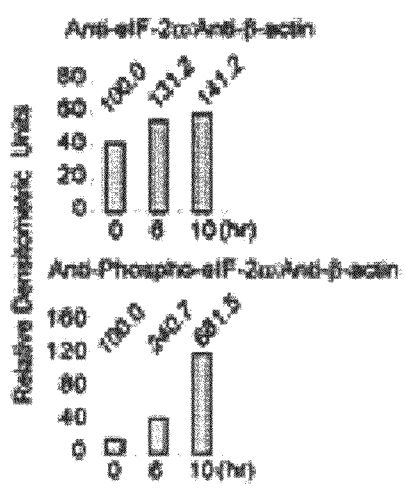

Phosphorylated eIF-2α was upregulated (681.5% at 10 hrs) in response to IFN-α stimulation, whereas eIF-2α was only upregulated in a modest manner (141.2% at 10 hrs) (FIG. 3B). Since the unconventional leucine start codon is enhanced in the presence of phosphorylated eIF-2α(17), the upregulated phosphorylated eIF-2α in response to IFN-α stimulation (23) might enhance MPD6 translation, which is mediated by the unconventional isoleucine start codon.

Figure 3C:
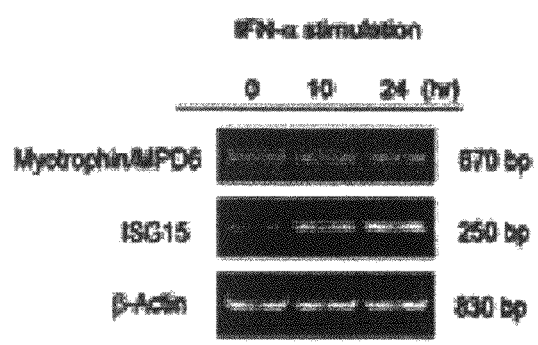
Figure 3C:
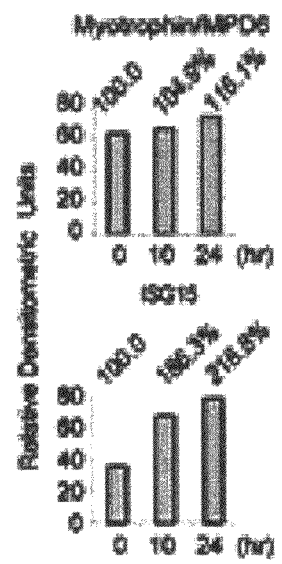
Figure 3D:
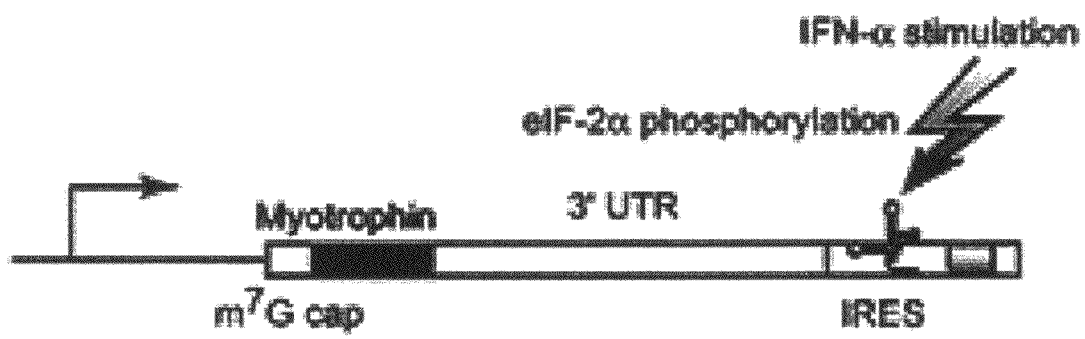

IRES-mediated translation or the transcription of myotrophin-MPD6 is the major mechanism for upregulation of MPD6 after IFN-α stimulation. As shown in FIG. 3C, as a positive control, the expression of ISG15 RNA transcripts was significantly upregulated (116.8%) in response to IFN-α stimulation (31), indicating the cells were appropriately stimulated with IFN-α. Under the same conditions, the transcription of myotrophin-MPD6 mRNA was increased only 16.1% after IFN-α stimulation. In contrast, the MPD6-IRES mediated translation of EGFP was significantly increased by 130% (FIG. 3A-1-24 hr and the lower left panel of FIG. 3A). Taken together, these results indicate that MPD-IRES mediated translation is the major mechanism for upregulation of MPD6 after IFN-α stimulation.

It is noteworthy that MPD6-IRES mediated enhanced protein expression by IFN-α (FIG. 3A-1) did not correlate well with lower detection rates of MPD6-specific antibodies in patients who received IFN-α therapy (FIG. 1D). This discrepancy was expected since the upregulated expression of tumor antigens is not the only determining mechanism for their increased immunogenicity (12).

Interferon-α

Interferon-α (IFN-α), a pleiotropic cytokine, is widely used in cancer therapy (1). IFN-α therapy induces a clinical remission with documented reversal of clonal hematopoiesis to polyclonal hematopoiesis (2) in polycythemia vera (PV) patients (3), thus making PV a model to study the antigenic mechanism of the cytokine-enhanced immune responses (1). Similarly, ~25% of patients with chronic myeloid leukemia (CML), another myeloproliferative disease (MPD), treated with IFN-α undergo a cytogenetic remission (4). In addition to its direct cytotoxic effects on tumors, IFN-α has been shown to enhance anti-tumor immune response (1). Cytogenetic response to IFN-α therapy in CML is often associated with therapy-related autoimmunity (5), indicating that anti-self antigen immune responses induced by IFN-α will play an important role in controlling these diseases. The mechanism of IFN-α regulation of the expression of self-antigens (4) remains largely unknown.

IFN-α has been shown to enhance anti-tumor immune response (4). However, the self-antigen targets and the mechanism of IFN-α inducing anti-tumor immune response remain poorly defined. The reversion of clonal to polyclonal hematopoiesis in PV patients who responded to IFN-α therapy has been reported (2). These studies have laid a foundation for definition of therapeutic immune responses in patients with PV. Further, current studies indicate that multiple genetic defects may be involved in the pathogenesis of PV (54), reflecting tumor heterogeneity and presumably antigen heterogeneity (55). Therefore, it would beneficial for the antigen-specific based vaccine and other therapeutic approaches to encompass a broader array of tumor antigens to affect broad subpopulations of tumor cells that may express different tumor antigens (55). The gain-of-function acquired somatic mutation (V617F) of the tyrosine kinase JAK2 has been identified in most patients with PV and other MPDs (56-60). It remains to be determined if the activating mutation of JAK2 may modulate the expression of tumor antigens and anti-tumor immune responses, a subject currently under investigation (61).

To determine the novel mechanisms underlying self-antigen immunogenicity, the Inventor focused on RNA transcription and processing. The canonical scanning mechanism has been utilized for the translation initiation of more than 90% mRNAs in eukaryotic cells in recruiting ribosomes at the capped 5' end of mRNAs (24). Internal ribosome entry sites (IRES) are highly structured regions located within the untranslated region that enable ribosomes to initiate translation effectively (24). It is estimated that up to 10% of all mRNAs have the capability to initiate translation by this mechanism (25). These mRNAs can utilize IRES to promote the translation of downstream cryptic cistron (24). It has become clear that IRESs are very important component of protein expression in various essential organismal and cellular processes including development, cell cycle and apoptosis (25).

SEREX

Development of SEREX has led to rapid identification of a large number of tumor antigens deposited in the SEREX database. In contrast, a modest number of tumor antigens have been targeted in tumor vaccines and immunotherapies (14). Several steps of analysis are Mandatory to evaluate SEREX-defined antigens before they become new target antigens for active immunotherapy, including expression analysis, and serological analysis with sera from tumor patients and normal individuals, etc. (62). As a result, a few tumor antigens have yet be exploited in immunotherapy. Demand for new antigen-specific immunotherapies and current technical problems all call for urgent development of new, high through-put technology in mapping immunodominant T cell antigen epitopes, characterization of more clinically targetable antigens from the database, and elucidation of novel mechanisms underlying the immunogenicity of tumor antigens, as is disclosed in the instant invention.

By applying the SEREX technique to screen a human testis expression cDNA library with sera from PV patients, the Inventor identified a novel SEREX antigen that elicits potent humoral immune responses in a subset of patients with MPD. The cryptic antigen peptides encoded by introns or UTRs can elicit T cell responses (19, 66), but also demonstrated that unconventional cryptic antigen peptides can elicit IgG antibody responses (23). The invention provides a novel cryptic antigen MPD6 and show that its expression is IRES-mediated. Since these unconventional antigens are small peptides, they require only minimal processing to yield the peptide sizes suitable for MHC class I, class II restricted, and antibody-recognized antigen epitopes in order to effectively expand self-antigen repertoire (18). In addition, although short peptide antigens may have the disadvantage of being presented in fewer MHC allelic molecules, they may possess an advantage of being not very immunogenic, which may lead to antigen-specific energy in patients with tumors (67). The upregulation of MPD6-IRES-initiated translation by IFN-α provides new insight into the mechanism of regulating the self-antigen repertoire in response to IFN-α. The demonstration of tumor associated antibody responses elicited by a novel IRES-mediated translation of unconventional antigen is the first such study in tumor immunology (68).

IFN-α treatment induces upregulation of numerous genes in tumor cells (69) and other cells (70). However, proteins upregulated by IFN-α may not necessarily all become self-tumor antigens (14). As discussed previously (20, 71), the overexpression of self-antigens must overcome the "threshold" of antigen concentration at which an immune response is initiated as Zinkernagel et al. recently suggested (72, 73). In addition, overexpressed antigens must access the antigen presentation pathway and immune system by the following mechanisms (74). First, overexpressed antigens may be released from damaged tumor cells due to spontaneous necrosis or apoptosis, and then become available in the extracellular environment for attack by the immune cells, potentially through cross-presentation (75, 76); second, tumor expressed antigens can translocate across the intracellular membranes (77) via binding to heat shock protein 70 and enter the membrane exosome for MHC class II antigen presentation pathway (78). Moreover, some other factors contributing to the immunogenicity of autoantigens and self-tumor antigens have also been proposed (79).

Translation

There are two mechanisms used by eukaryotic cells to initiate translation, the classical 7-methyl guanosine cap-dependent scanning mechanism and internal ribosome entry site (IRES) (24). IRESs are diverse cis-acting RNA sequences which are able to mediate internal entry of the 40S ribosomal subunit directly onto an AUG or other start codons (17) of eukaryotic and viral messenger RNAs (82). IRESs are often found in essential mRNAs encoding regulatory proteins (transcription factors, growth factors, and kinases) (25). IRES activity can be modulated in response to mitotic stimuli, hypoxia and other stimuli, p38 MAPK signaling (83), GM-CSF, and IL-3 via the PI3 kinase pathway (84), which indicate that IRES-containing transcripts (85) are important determinants of cellular proliferation and/or differentiation (82).

Identification of novel cryptic self-antigen peptides improves our understanding of the self-antigen repertoire (19). The activation of PKR by IFN-α could induce hepatitis C virus internal ribosome entry site (IRES)-dependent mRNA translation from dicistronic constructs (86), analogous to our observation that the MPD6-IRES mediated EGFP translation was increased in responses to IFN-α stimulation. IFN-α-induced, double-stranded (ds) RNA-activated PKR is a key mediator of the antiviral and anti-proliferative effects of IFN (87), thus IFN-α activates IRES-dependent translation of MPD6.

MPD6 Nucleic Acids

One aspect of the present invention is the polynucleotide sequences essentially as set forth in SEQ ID NO: 1, the complement of these sequences, the RNA versions of both DNA strands and the information otherwise contained within the linear sequence of these polynucleotide sequences, and fragments thereof. The polynucleotide encoding MPD6 is exemplified by SEQ ID NO: 1. In the case of nucleic acid segments, sequences for use with the present invention are those that have greater than about 50 to 60% homology with any portion of the polynucleotide sequences described herein, sequences that have between about 61% and about 70%; sequences that have between about 71 and about 80%; or between about 81% and about 90%; or between 91% and about 99%; or which contain nucleotides that are identical, functionality equivalent, or functionally irrelevant, with respect to the nucleotides present in SEQ ID NO: 1 are considered to be essentially similar. Also encompassed within the present invention are nucleic acids that encode polypeptides that are at least 40% identical or similar to the amino acid sequences shown in SEQ ID NO: 2.

The invention also encompasses other nucleic acids or nucleic acid like molecules that are sufficient in any regard to mimic, substitute for, or interfere with the MPD6 polynucleotide sequences, as exemplified by SEQ ID NO: 1, or fragments thereof. It will also be understood that the nucleic acid and amino acid sequences may include additional residues, such as additional 5'- or 3'-sequences, and yet still be essentially as set forth in one of the sequences disclosed herein, so long as the sequence meets the criteria set forth, including the maintenance of functionality, or for the purpose of engineering altered functionality with respect to MPD6.

Included within the invention are DNA or RNA segments including oligonucleotides, polynucleotides and fragments thereof, including DNA or RNA or nucleic acid-like sequences of genomic or synthetic origin, single or double stranded. The invention includes nucleic acid molecules, or nucleic acid-like molecules that are able to hybridize to the sequences in SEQ ID NO: 1, under stringent or under permissive hybridization conditions, or to the complement of said sequences.

The invention also includes oligonucleotide, or oligonucleotide-like sequences such as phosphorthioate, or peptide nucleic acid sequences, which possess sufficient similarity with the sequences disclosed herein such that they are able to stably hybridize to the disclosed sequences, or their complements. Such sequences may be intended as antisense regulators of gene expression, or for the selective amplification or extension of adjoining sequences, for instance by PCR using a given annealing temperature, as would be determined by someone skilled in the art. In addition to the sequences disclosed here, related sequences in other organisms, or homologs, will be readily identified by hybridization using the present sequences. Similar techniques will also apply to the identification of mutant alleles, polymorphisms, deletions, insertions, and so forth, in genomic and cDNA sequences. Whole or partial sequences referred to above may also be identified and isolated using techniques that involve annealing of short oligonucleotides to complementary sequences, such as those as might be present in the genomic DNA of a particular organism, or in genomic or cDNA, including expression cDNA, libraries. Thus, PCR is used to obtain DNA sequences homologous to, and which lie between, two primers, usually between 15 to 30 nucleotides which have annealing temperatures typically between 60-80 degrees Celsius may be substantially purified.

It will be understood that this invention is not limited to the particular nucleic acid sequences presented herein. Recombinant vectors, including for example plasmids, phage, viruses, and other sequences, and isolated DNA or RNA segments may therefore variously include the MPD6 gene sequences or their complements, and coding regions, as well as those that may bear selected alterations or modifications that nevertheless include MPD6 segments or may encode biologically or experimentally relevant amino acid sequences. Such sequences may be created by the application of recombinant DNA technology, where changes are engineered based on the consideration of the nucleotides or amino acids being exchanged, deleted, inserted, fused, or otherwise modified.

MPD6 Proteins and Polypeptides

One aspect of the invention is the protein, polypeptide, oligopeptide, or amino acid sequences or fragments thereof, of MPD6, essentially as set forth in SEQ ID NO: 2. The MPD6 polypeptide is exemplified by SEQ ID NO: 2. Sequences that have greater than about 40-50% homology with any portion of the amino acid sequences described herein, sequences that have between about 51% and about 60%; sequences that have between about 61% and about 70% sequences that have between about 70 and about 80%; or between about 81% and about 90%; or between 91% and about 99%; or those that contain amino acids that are identical, functionally equivalent, or functionally irrelevant, for instance those specified by conservative, evolutionarily conserved, and degenerate substitutions, with respect to the amino acid sequences presented in SEQ ID NO: 2 are included. The invention thus applies to MPD6 polypeptide sequences, or fragments thereof, and nucleic acids which encode such polypeptides, such as those of other species. Reference is particularly, but not exclusively, made to the conserved regions of MPD6, in contrast to similarity throughout the entire length. The invention thus encompasses amino acid sequences, or amino acid-like molecules, that are sufficient in any regard to mimic, substitute for, or interfere with the MPD6 amino acid sequences, or fragments thereof.

The invention encompasses MPD6 amino acid sequences that have been altered in any form, either through the use of recombinant engineering, or through post-translational or chemical modifications, including those that may be produced by natural, biological, artificial, or chemical methods. Naturally, it will be understood that this invention is not limited to the particular amino acid sequences presented herein. Altered amino acid sequences include those which have been created by the application of recombinant technology such that specific residues, regions, or domains have been altered, and which may be functionally identical, or which may possess unique biological or experimental properties with regards to function or interactions with natural and artificial ligands.

For instance such modifications may confer longer or shorter half-life, reduced or increased sensitivity to ligands that modify function, ability to detect or purify polypeptides, solubility, and so forth. Alternatively, such sequences may be shorter oligopeptides that possess an antigenic determinant, or property that interferes, or competes, with the function of a larger polypeptide, and those that affect interactions between MPD6 other proteins, other nucleic acid regions, and other proteins. Such sequences may be created by the application of the nucleotides or amino acids being exchanged, deleted, inserted, fused, or otherwise modified. Likewise, the current invention within, the sequences that may be naturally present as extensions of, or insertions within, the sequences disclosed herein, including alternative or longer N- and C-terminal sequences, or alternatively spliced protein isoforms.

Production and purification of polypeptides may be achieved in any of a variety of expression systems known to those skilled in the art, including recombinant DNA techniques, genetic recombination, and chemical synthesis. For instance, expression in prokaryotic cells may be achieved by placing protein coding nucleic sequences downstream of a promoter, such as T7, T3, lacI, lacZ, trp, or other cellular, viral, or artificially modified promoters including those that may be inducible by IPTG, tetracycline, maltose, and so forth. Such promoters are often provided for in commercially available recombinant DNA vectors such as pRSET ABC, pBluescript, pKK223-3, and others, or are easily constructed to achieve such a purpose, and often include the presence of multiple cloning sites (MCS) to facilitate typically contain efficient ribosome binding sites, and in some cases transcription termination signals.

Peptides, oligopeptides and polypeptides may also be produced by chemical synthesis, for instance solid phase techniques, either manually or under automated control such as Applied Biosystems 431 peptide synthesizer (Perkin Elmer). After synthesis, such molecules are often further purified by preparative high performance liquid chromatography. Thus, the invention provides methods for the production of epitopes for antibody production, or the production of small molecules that enhance or interfere with a specific function or interaction of the MPD6 polypeptides.

Methods to produce and purify said polypeptides in eukaryotic systems are widely available and understood by those proficient in the art. Cells for such production are known to include yeast and other fungi, *Drosophila* and Sf9 cells, cells of other higher eukaryotic organisms such as HeLa, COS, CHO and others, as well as plant cells. Similarly, expression could be achieved in prokaryotic or eukaryotic extracts that are able to translate RNAs into proteins, such as rabbit reticulocyte lysates.

Vectors

Numerous expression systems exist that comprise at least a part or all of the compositions discussed above. Prokaryote- and/or eukaryote-based systems can be employed for use with the present invention to produce nucleic acid sequences, or their cognate polypeptides, proteins and peptides. Many such systems are commercially and widely available.

The insect cell/baculovirus system can produce a high level of protein expression of a heterologous nucleic acid segment, such as described in U.S. Pat. Nos. 5,871,986, 4,879,236, both herein incorporated by reference, and which can be bought, for example, under the name MAXBAC®. 2.0 from INVITROGEN® and BACPACK® BACULOVIRUS EXPRESSION SYSTEM FROM CLONTECH.

Vectors may be of bacterial origin, which may comprise a promoter of a bacteriophage such as phage or T7 which is capable of functioning in the bacteria. In one of the most widely used expression systems, the nucleic acid encoding the MPD6 may be transcribed from the vector by T7 RNA polymerase (Studier et al, Methods in Enzymol. 185: 60-89, 1990). In the *E. coli* BL21 (DE3) host strain, used in conjunction with pET vectors, the T7 RNA polymerase is produced from the 1-lysogen DE3 in the host bacterium, and its expression is under the control of the IPTG inducible lac UV5 promoter. This system has been employed successfully for over-production of many proteins. Alternatively, the polymerase gene may be introduced on a lambda phage by infection with an int-phage such as the CE6 phage, which is commercially available (Novagen, Madison, USA). Other vectors include vectors containing the lambda PL promoter such as PLEX® (Invitrogen, NL), vectors containing the trc promoters such as pTrcH is Xpress® (Invitrogen), or pTrc99 (Pharmacia Biotech, SE), or vectors containing the tac promoter such as pKK223-3 (Pharmacia Biotech), or PMAL (New England Biolabs, MA, USA).

One of skill in the art will understand that cloning also requires the step of transforming a host cell with a recombinant nucleic acid molecule. A host cell is "transformed" by a nucleic acid when the nucleic acid is translocated into the cell from the extracellular environment. Any method of transferring a nucleic acid into the cell may be used; the term, unless otherwise indicated herein, does not imply any particular method of delivering a nucleic acid into a cell, nor that any particular cell type is the subject of transfer. For example, bacterial host cells, such as *E. coli* HB101, can be transformed by electroporation using any commercially-available electroporation apparatus known in the art, such as a GenePulser apparatus (Bio-Rad, Hercules, Calif.). In one embodiment, mammalian cells, such as BHK-21 cells or Vero cells (ATCC CCL-81), are transformed with a recombinant plasmid containing a cloned cDNA by the method of "transfection." The term "transfection" refers to the transfer of genetic material into a eukaryotic cell, such as a mammalian cell, from the external environment of the cell.

One of skill in the art will appreciate the variety of methods of transfection that are available in the art. Such methods include the nucleic acid/CaPO4 co-precipitation method, the diethylaminoethyl (DEAE)-dextran method, the polybrene method, the cationic liposome method ("lipofection"), the electroporation method, the microinjection method, and the microparticle bombardment method. A description of transfection methods can be found in M. A. Aitken et al., Molecular Biomethods Handbook, Chapter 20, p. 235-250.

According to another embodiment of the instant invention, in vitro transcription is carried out on a recombinant plasmid carrying a cloned cDNA of the invention, under the control of an expressible promoter (i.e., a promoter which is effectively enabled or activated in vitro in the presence of corresponding transcription factors and RNA polymerase). The transcription process generates a fully-infectious mRNA transcript that can be used to transfect (i.e., infect) a cell host, such as BHK-21 (hamster kidney cells) or Vero cells. In one embodiment, the cDNA is operably linked with the bacteriophage transcriptional promoter, T7; to enable the in vitro transcription of the cDNA using bacteriophage T7 DNA-dependent RNA polymerase. One of ordinary skill in the art will appreciate that any suitable promoter, such as, for example, SP6, T3, any bacterial, viral, phage, or eukaryotic promoter, for controlling the transcription of, for example, the MPD6 gene, or fragment thereof, and for controlling the expression of a nucleotide sequence encoding a reporter is contemplated by the present invention. It will be appreciated that the promoter is typically selected from promoters which are functional in mammalian cells susceptible to infection by the MPD6 gene, or fragment thereof, encoding sequences of the invention, although prokaryotic or phage promoters and promoters functional in other eukaryotic cells may be used. The promoter is typically derived from promoter sequences of viral or eukaryotic genes. For example, it may be a promoter derived from the genome of a cell in which expression or transcription of, for example, the MPD6 gene, or fragment thereof, encoding sequence or construct is to occur.

With respect to eukaryotic promoters, they may be promoters that function in a ubiquitous manner (such as promoters of α-actin, β-actin, tubulin) or, alternatively, a tissue-specific manner (such as promoters of the genes for pyruvate kinase). Tissue-specific or cell-specific promoters specific for lymphocytes, dendritic cells, skin, brain cells and epithelial cells, for example the CD2, CD11c, keratin 14, Wnt-1 and Rhodopsin promoters, respectively. Preferably the epithelial cell promoter SPC is used. They may also be promoters that respond to specific stimuli, for example promoters that bind steroid hormone receptors. Viral promoters may also be used, for example the Moloney murine leukaemia virus long terminal repeat (MMLV LTR) promoter, the rous sarcoma virus (RSV) LTR promoter, the human cytomegalovirus (CMV) IE promoter, or SV40 promoter.

It may also be advantageous for the promoters to be inducible so that the levels of expression of, for example, the MPD6 gene, or fragment thereof encoding sequence can be regulated during the life-time of the cell. Inducible means that the levels of expression obtained using the promoter can be regulated.

In addition, any of these promoters may be modified by the addition of further regulatory sequences, for example enhancer sequences. Chimeric promoters may also be used comprising sequence elements from two or more different promoters described above. It will be appreciated that the sources of promoter sequences, which typically can be retrieved using recombinant techniques from different cloning vectors and plasmids, etc., can be obtained from commercial sources, such as, NEW ENGLAND BIOLABS, INC. (MA), PROMEGA CORPORATION (WI), or BD BIOSCIENCES (CA), or from the laboratories of academic research groups upon request.

The invention also relates to cells which contain such recombinant constructs, where the host cell refers to mammalian, plant, yeast, insect, or other eukaryotic cells, or to prokaryotic, or archae, and vectors that are designed for a given host. Promoter-vector combinations could be chosen by a person skilled in these arts. In some cases, the desired outcome may not be protein, but RNA, and recombinant vectors would include those with inserts present in either forward or reverse orientations.

Many of the vectors and hosts have specific features that facilitate expression or subsequent purification. For instance DNA sequences to be expressed as proteins often appear as fusion with unrelated sequences that encode polyhistidine tags, or HA, FLAG, myc and other epitope tags for immunochemical purification and detection, or phosphorylation sites, or protease recognition sites, or additional protein domains such as glutathione S-transferase (GST), maltose binding protein (MBP), and so forth which facilitate purification. Vectors may also be designed which contain elements for polyadenylation, splicing and termination, such that incorporation of naturally occurring genomic DNA sequences that contain introns and exons can be produced and processed, or such that unrelated introns and other regulatory signals require RNA processing prior to production of mature, translatable RNAs. Proteins produced in the systems described above could be subject to a variety of post-translational modifications, such as glycosylation, phosphorylation, nonspecific or specific proteolysis or processing.

Purification of MPD6, or variants produced as described above can be achieved by any of several widely available methods. Cells may be subject to freeze-thaw cycles or sonication to achieve disruption, or may be fractionated into subcellular components prior to further purification. Purification may be achieved by one or more techniques such as precipitation with salts or organic solvents, ion exchange, hydrophobic interaction, HPLC and FPLC chromatographic techniques. Affinity chromatographic techniques could include the use of polyclonal or monoclonal antibodies raised against the expressed polypeptide, or antibodies raised against or available for an epitopic tag such as HA or FLAG. Similarly, purification can be aided by affinity chromatography using fusions to the desired proteins such as GSH-affinity resin, maltose affinity resin, carbohydrate (lectin) affinity resin or, in a one embodiment, Ni-affinity resin, and so forth. In some instances purification is achieved in the presence of denaturing agents such as urea or guanidine, and subsequent dialysis techniques may be required to restore functionality, if desired.

Any method of in vitro transcription known to one of ordinary skill in the art is contemplated by the instant invention. It will be understood that the method of in vitro transcription of a DNA sequence relies on the operable linkage to an appropriate promoter and that the cognate RNA polymerase is used to direct transcription of the DNA starting at the promoter sequence. It will be further appreciated that the RNA polymerase and promoter can be of bacterial, eukaryotic, or viral (including bacteriophage) origin. Bacteriophage-RNA polymerases are very robust, and the availability of purified recombinant proteins facilitates the generation of large quantities of RNA from cloned cDNA sequences. In contrast, eukaryotic in vitro transcription systems yield relatively small quantities of RNA. Bacteriophage-RNA polymerases, such as from bacteriophages SP6, T7, and T3, are especially suitable for the generation of RNA from DNA sequences cloned downstream of their specific promoters because, first, their promoters are small and easily incorporated into plasmid vectors and second, the polymerases are quite specific for their cognate promoters, which results in very little incorrect transcriptional initiation from DNA templates. Any suitable promoter, however, is contemplated by the instant invention, including, for example, bacterial, phage, viral, and eukaryotic promoters. Strong termination sequences are not available for these polymerases so that DNA templates can be linearized with a restriction enzyme 3' to the desired end of the RNA transcript and the polymerase is forced to stop at this point-a process referred to as "run-off" transcription. A full description of in vitro transcription can be found in M. A. Aitken et al., Molecular Biomethods Handbook, Chapter 26, p. 327-334 and Sambrook, J. and D. W. Russell, Molecular Cloning: A Laboratory Manual, Third Edition (2001).

The invention provides a dual luciferase reporter system for measuring recoding efficiencies in vivo or in vitro from a single construct see U.S. Pat. No. 6,143,502 (Grentzmann et al.). For example, the firefly luciferase gene (fluc) has been cloned behind the renilla luciferase gene (rluc) into an altered vector pRL-SV40 vector (Promega Corp., Madison, Wis.; catalog no. TB239). Other reporter genes may also be used, for example, green fluorescent protein, and variants thereof. Expression features for initiation and termination of transcription and translation, as well as the nature of the two reporter genes (short enough to be efficiently synthesized in an in vitro translation system), allow application of the same reporter construct for in vivo and in vitro applications. Between the 5' reporter (rluc) and the 3' reporter (flue) two alternative polylinkers have been inserted, yielding p2luc and p2luci. The p2luc polylinker has restriction sites for digestion with SalI, BamHI, and SacI, whereas the p2luci polylinker has restriction sites for digestion with SalI, ApaI, BglII, Eco47III, BamHI, SmaI, and SacI. The assay using these reporter plasmids combines rapidity of the reactions with very low background levels and provides a powerful assay. In vitro experiments can be performed in 96-well microtiter plates, and in vivo experiments can be performed in 6-well culture dishes. This makes the dual-luciferase assay suitable for high throughput screening approaches.

Host Cells

As used herein, the terms "cell," "cell line," and "cell culture" may be used interchangeably. All of these term also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organisms that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny.

An appropriate host can be determined by one of skill in the art based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE®. Competent Cells and SOLOPACK® Gold Cells (STRATAGENE®, La Jolla). Alternatively, bacterial cells such as E. coli LE392 could be used as host cells for phage viruses.

Examples of eukaryotic host cells for replication and/or expression of a vector include HeLa, NIH3T3, Jurkat, 293, Cos, CHO, Saos, and PC12, etc. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Diagnostic Systems and Kits

A diagnostic system in kit form of the present invention includes, in an amount sufficient for at least one assay, a polypeptide, antibody composition or monoclonal antibody composition of the present invention, as a packaged reagent. Instructions for use of the packaged reagent are also typically included.

As used herein, the term "package" refers to a solid matrix or material such as glass, plastic, paper, foil and the like capable of holding within fixed limits a polypeptide, antibody composition or monoclonal antibody composition of the present invention. Thus, for example, a package can be a glass vial used to contain milligram quantities of a contemplated polypeptide or it can be a microtiter plate well to which microgram quantities of a contemplated polypeptide have been operatively affixed, i.e., linked so as to be capable of being immunologically bound by an antibody. "Instructions for use" typically include a tangible expression describing the reagent concentration or at least one assay method parameter such as the relative amounts of reagent and sample to be admixed, maintenance time periods for reagent/sample admixtures, temperature, buffer conditions and the like.

In preferred embodiments, a diagnostic system of the present invention further includes a label or indicating means capable of signaling the formation of a complex containing a polypeptide or antibody molecule of the present invention. The word "complex" as used herein refers to the product of a specific binding reaction such as an antibody-antigen or receptor-ligand reaction. Exemplary complexes are immunoreaction products.

As used herein, the terms "label" and "indicating means" in their various grammatical forms refer to single atoms and molecules that are either directly or indirectly involved in the production of a detectable signal to indicate the presence of a complex. Any label or indicating means can be linked to or incorporated in an expressed protein, polypeptide, or antibody molecule that is part of an antibody or monoclonal antibody composition of the present invention, or used separately, and those atoms or molecules can be used alone or in conjunction with additional reagents such labels are themselves well-known in clinical diagnostic chemistry and constitute a part of this invention only insofar as they are utilized with otherwise novel proteins methods and/or systems. The labeling means can be a fluorescent labeling agent that chemically binds to antibodies or antigens without denaturing them to form a fluorochrome (dye) that is a useful immunofluorescent tracer. Suitable fluorescent labeling agents are fluorochromes such as fluorescein isocyanate (FIC), fluorescein isothiocyante (FITC), 5-dimethylamine-1-naphthalenesulfonyl chloride (DANSC), tetramethylrhodamine isothiocyanate (TRITC), lissamine, rhodamine 8200 sulphonyl chloride (RB 200 SC) and the like. A description of immunofluorescence analysis techniques is found in DeLuca, "Immunofluorescence Analysis", in Antibody As a Tool, Marchalonis, et al., eds., John Wiley & Sons, Ltd., pp. 189-231 (1982), which is incorporated herein by reference.

In preferred embodiments, the indicating group' is an enzyme, such as horseradish peroxidase (HRP), glucose oxidase, or the like. In such cases where the principal indicating group is an enzyme such as HRP or glucose oxidase, additional reagents are required to visualize the fact that a receptor-ligand complex (immunoreactant) has formed. Such additional reagents for HRP include hydrogen peroxide and an oxidation dye precursor such as diaminobenzidine. An additional reagent useful with glucose oxidase is 2,2'-azino-di-(3-ethyl-benzthiazoline-G-sulfonic acid) (ABTS).

Radioactive elements are also useful labeling agents and are used illustratively herein. An exemplary radiolabeling agent is a radioactive element that produces gamma ray emissions. Elements which themselves emit gamma rays, such as $^{124}I$, $^{125}I$, $^{128}I$, $^{132}I$ and $^{51}Cr$ represent one class of gamma ray emission-producing radioactive element indicating groups. Particularly preferred is $^{125}I$. Another group of useful labeling means are those elements such as $^{11}C$, $^{18}F$, $^{15}O$ and $^{13}N$ which themselves emit positrons. The positrons so emitted produce gamma rays upon encounters with electrons present in the animal's body. Also useful is a beta emitter, such $^{111}$indium or $^{3}H$.

The linking of labels, i.e., labeling of, polypeptides and proteins is well known in the art. For instance, antibody molecules produced by a hybridoma can be labeled by metabolic incorporation of radioisotope-containing amino acids provided as a component in the culture medium. See, for example, Galfre et al., Meth. Enzymol., 73:3-46 (1981). The techniques of protein conjugation or coupling through activated functional groups are particularly applicable. See, for example, Aurameas, et al., Scand. J. Immunol., Vol. 8 Suppl.

7:7-23 (1978), Rodwell et al., Biotech., 3:889-894 (1984), and U.S. Pat. No. 4,493,795, which are all incorporated herein by reference.

The diagnostic kits of the present invention can be used in an "ELISA" format to detect, for example, the presence or quantity of MPD6 in a body fluid sample such as serum, plasma, or urine, etc. "ELISA" refers to an enzyme-linked immunosorbent assay that employs an antibody or antigen bound to a solid phase and an enzyme-antigen or enzyme-antibody conjugate to detect and quantify the amount of an antigen or antibody present in a sample. A description of the ELISA technique is found in Chapter 22 of the 4th Edition of Basic and Clinical Immunology by D. P. Sites et al., published by Lange Medical Publications of Los Altos, Calif. in 1982 and in U.S. Pat. Nos. 3,654,090; 3,850,752; and 4,016,043, which are all incorporated herein by reference.

Thus, in preferred embodiments, a polypeptide, antibody molecule composition or monoclonal antibody molecule composition of the present invention can be affixed to a solid matrix to form a solid support that comprises a package in the subject diagnostic systems.

The reagent is typically affixed to the solid matrix by adsorption from an aqueous medium although other modes of affixation, well known to those skilled in the art, can be used. Useful solid matrices are also well known in the art. Such materials are water insoluble and include cross-linked dextran; agarose; beads of polystyrene beads about 1 micron to about 5 millimeters in diameter; polyvinyl chloride, polystyrene, cross-linked polyacrylamide, nitrocellulose- or nylon-based webs such as sheets, strips or paddles; or tubes, plates or the wells of a microtiter plate such as those made from polystyrene or polyvinylchloride.

The packaging materials discussed herein in relation to diagnostic systems are those customarily utilized in diagnostic systems. Such materials include glass and plastic (e.g., polyethylene, polypropylene and polycarbonate) bottles, vials, plastic and plastic-foil laminated envelopes and the like. In one embodiment a diagnostic system of the present invention is useful for assaying for the presence of MPD6. Such a system comprises, in kit form, a package containing an antibody to MPD6.

Vaccine

Another aspect of the invention relates to a method for inducing an immunological response in an individual, particularly a mammal which comprises inoculating the individual with, for example, MPD6, or a fragment or variant thereof. Also provided are methods whereby such immunological response slows bacterial replication. Yet another aspect of the invention relates to a method of inducing immunological response in an individual which comprises delivering to such individual a nucleic acid vector to direct expression of, for example, an MPD6, or a fragment or a variant thereof, for expressing, for example, MPD6, or a fragment or a variant thereof in vivo in order to induce an immunological response, such as, to produce antibody and/or T cell immune response, including, for example, cytokine-producing T cells or cytotoxic T cells, to protect said individual from disease, whether that disease is already established within the individual or not. One way of administering the gene is by accelerating it into the desired cells as a coating on particles or otherwise. Such nucleic acid vector may comprise DNA, RNA, a modified nucleic acid, or a DNA/RNA hybrid.

A further aspect of the invention relates to an immunological composition which, when introduced into an individual capable or having induced within it an immunological response, induces an immunological response in such individual to, for example, an MPD6 gene, or protein coded therefrom, wherein the composition comprises, for example, a recombinant MPD6 gene, or protein coded therefrom comprising DNA which codes for and expresses an antigen of said MPD6 or protein coded therefrom. The immunological response may be used therapeutically or prophylactically and may take the form of antibody immunity or cellular immunity such as that arising from CTL or CD4+T cells.

In an exemplary embodiment, an MPD6 polypeptide or a fragment thereof may be fused with co-protein which may not by itself produce antibodies, but is capable of stabilizing the first protein and producing a fused protein which will have immunogenic and protective properties. Thus fused recombinant protein, preferably further comprises an antigenic co-protein, such as lipoprotein D from *Hemophilus influenzae*, Glutathione-S-transferase (GST) or beta-galactosidase, relatively large co-proteins which solubilize the protein and facilitate production and purification thereof. Moreover, the co-protein may act as an adjuvant in the sense of providing a generalized stimulation of the immune system. The co-protein may be attached to either the amino or carboxy terminus of the first protein.

Provided by this invention are compositions, particularly vaccine compositions, and methods comprising the polypeptides or polynucleotides of the invention and immunostimulatory DNA sequences, such as those described in Sato, Y. et al. Science 273: 352 (1996).

The invention also includes a vaccine formulation which comprises an immunogenic recombinant protein of the invention together with a suitable carrier, the invention also provides that these formulations may be provided in kit form. The vaccine may for example, be administered parenterally, including, for example, administration that is subcutaneous, intramuscular, intravenous, or intradermal. Formulations suitable for parenteral administration include aqueous and non-aqueous sterile injection solutions which may contain anti-oxidants, buffers, bacteriostats and solutes which render the formulation isotonic with the bodily fluid, preferably the blood, of the individual; and aqueous and non-aqueous sterile suspensions which may include suspending agents or thickening agents. The formulations may be presented in unit-dose or multi-dose containers, for example, sealed ampules and vials and may be stored in a freeze-dried condition requiring only the addition of the sterile liquid carrier immediately prior to use. The vaccine formulation may also include adjuvant systems for enhancing the immunogenicity of the formulation, such as oil-in water systems and other systems known in the art. The dosage will depend on the specific activity of the vaccine and can be readily determined by routine experimentation.

While the invention has been described with reference to certain MPD6 protein, it is to be understood that this covers fragments of the naturally occurring protein and similar proteins with additions, deletions or substitutions which do not substantially affect the immunogenic properties of the recombinant protein.

Target Antigens

An embodiment of the present invention relates to an antibody that binds to a MPD6 protein. A typical amino acid sequence of MPD6 protein is shown in SEQ ID NO: 2. That is, an antibody according to the first embodiment of the present invention is preferably an antibody that specifically binds to, for example, the MPD6 polypeptide. Full length MPD6 protein is exemplified in SEQ ID NO: 2, and variants, fragments, muteins, etc., and those proteins derived from this protein. It is known that humans have a diversity of allele mutations and those proteins with one or more amino acids substituted, deleted, inserted, or added are also included in the MPD6 protein. However, it is not limited to these. It is known that humans have a diversity of allele mutations and those proteins with one or more amino acids substituted, deleted, inserted, or added are also included in the MPD6 protein. However, it is not limited to these.

Fragments of the MPD6 protein may serve as the target antigen for the antibody binding. These antigen fragments may be about 6, 7, 8, 9, 10, 11, 12, 13, 14, 15, 16, 17, 18, 19, or 20 amino acids in length. The antigen fragments may by about 10, 20, 30, 40, 50, or 100 amino acids in length. The antibody of the present invention may be either a polyclonal antibody or a monoclonal antibody. To specifically detect a high molecular weight soluble MPD6 protein, it is desirable to use antibodies to certain limited epitopes and hence monoclonal antibodies are preferable. Molecule species are not particularly limited. Immunoglobulins of any class, subclass or isotype may be used.

Antibodies and Antibody Compositions

Additionally, the present invention includes a purified antibody produced in response to immunization with MPD6, as well as compositions comprising this purified antibody.

Antibodies refer to single chain, two-chain, and multi-chain proteins and glycoproteins belonging to the classes of polyclonal, monoclonal, chimeric, and hetero immunoglobulins; it also includes synthetic and genetically engineered variants of these immunoglobulins. "Antibody fragment" includes Fab, Fab', F(ab')2, and Fv fragments, as well as any portion of an antibody having specificity toward a desired target epitope or epitopes. A humanized antibody is an antibody derived from a non-human antibody, typically murine, that retains or substantially retains the antigen-binding properties of the parent antibody but which is less immunogenic in humans, U.S. Pat. No. 5,530,101, incorporated herein by reference in its entirety.

An antibody composition of the present invention is typically produced by immunizing a laboratory mammal with an inoculum of the present invention and to thereby induce in the mammal antibody molecules having the appropriate polypeptide immunospecificity. The polyclonal antibody molecules are then collected from the mammal and isolated to the extent desired by well known techniques such as, for example, by immunoaffinity chromatography. The antibody composition so produced can be used in, inter alia, the diagnostic methods and systems of the present invention to detect MPD6 in a body sample.

Monoclonal antibody compositions are also contemplated by the present invention. A monoclonal antibody composition contains, within detectable limits, only one species of antibody combining site capable of effectively binding MPD6. Thus, a monoclonal antibody composition of the present invention typically displays a single binding affinity for MPD6 even though it may contain antibodies capable of binding proteins other than MPD6. Suitable antibodies in monoclonal form, typically whole antibodies, can also be prepared using hybridoma technology described by Niman et al., Proc. Natl. Sci., U.S.A., 80:4949-4953 (1983), which description is incorporated herein by reference. Briefly, to form the hybridoma from which the monoclonal antibody composition is produced, a myeloma or other self-perpetuating cell line is fused with lymphocytes obtained from the spleen of a mammal hyperimmunized with a polypeptide of this invention.

The antibody compositions produced by the above method can be used, for example, in diagnostic and therapeutic modalities wherein formation of an MPD6-containing immunoreaction product is desired.

Diagnostic Use

In another embodiment of the present invention, measurement of MPD6, or proteins which are immunologically related to MPD6, can be used to detect and/or stage a disease or disorder in a subject. The measured amount of the soluble molecule or of the total marker is compared to a baseline level. This baseline level can be the amount which is established to be normally present in the body fluid of subjects with various degrees of the disease or disorder. An amount present in the body fluid of the subject which is similar to a standard amount, established to be normally present in the body fluid of the subject during a specific stage of the disease or disorder, is indicative of the stage of the disease in the subject. The baseline level could also be the level present in the subject prior to the onset of disease or the amount present during remission of disease, or from individuals not afflicted with the disease or condition.

The present invention also provides for the detection or diagnosis of disease or the monitoring of treatment by measuring the amounts of MPD6 transcript or peptide in a sample before and after treatment, and comparing the two measurements. The change in the levels of the markers relative to one another can be an improved prognostic indicator. A comparison of the amounts of a total marker with the amount of intra-cytoplasmic marker or membrane-bound marker is also envisioned.

The present invention provides a method for monitoring the effect of a therapeutic treatment on a subject who has undergone the therapeutic treatment. This method comprises measuring at suitable time intervals the amount of a soluble molecule or soluble fragment thereof, or the amount of MPD6 or fragment thereof. Any change or absence of change in the amount of the soluble molecule or in the amount of the MPD6 can be identified and correlated with the effect of the treatment on the subject. In a specific embodiment of the invention, soluble molecules immunologically related to MPD6 can be measured in the serum of patients by a sandwich enzyme immunoassay (for an example) in order to predict disease prognosis, for example, in viral infections, inflammation, autoimmune diseases, and tumors, or to monitor the effectiveness of treatments such as anti-viral administration.

The invention will be illustrated in more detail with reference to the following Examples, but it should be understood that the present invention is not deemed to be limited thereto.

EXAMPLES

Example 1

Serum Samples

Serum samples were obtained from the patients with PV and CML receiving IFN-α therapy enrolled into Temple University, Baylor College of Medicine, Cornell Medical Center, and M. D. Anderson Cancer Center Institutional Review Board-approved protocols (2). Serum samples from patients with hormone refractory advanced prostate cancer were generously provided by Dr. P. Kantoff from Harvard University (7).

Example 2

Transcriptional Based X-Chromosome Inactivation Clonality Assay (2)

To examine the clonality of hematopoietic cells in patients with PV before and after IFN-α therapy, the mRNA expression of five X-chromosome exonic polymorphic genes (MPP1, IDS, G6PD, BTK and FHL1) in platelets and granulocytes from the peripheral blood was detected using single-stranded conformation polymorphism (SSCP) analysis as previously described (2).

Example 3

Human Testis cDNA Library Screening by SEREX

The library screening was performed as described previously (6, 23). DNA sequencing was performed by SeqWright (Houston, Tex.).

Example 4

Bioinformatic Analyses

Sequence analyses were performed using the NCBI-GenBank databases, NCBI-conserved domain databases, and the PROSITE analysis to determine whether cloned sequences were related or identical to genes, proteins, or protein domains in the databases (21). The gene organizations, such as intron-exon structure and chromosome location, were analyzed by searching in the NCBI-AceView website (21). The expression of studied genes was determined by the Northern blots. The cis-acting regulatory elements in 3' untranslated region (3'UTR) were analyzed using the IRES and the UTR websites (27) with generous support of Dr. Sabino Liuni at the Bioinformatics and Genomic Group in Italy. The secondary structures of RNAs were predicted by using the MFOLD-Zuker (28) and the Vienna RNA (29) web-based algorithms.

Example 5

Northern Blot

Multiple tissue Northern blots were performed with purified polyadenylated RNA (Ambion, Austin, Tex.) as previously reported (7).

Example 6

Peptide Synthesis and Peptide ELISA

The MPD6 specific peptide, N-IVQIQHLNIPSSSSTH-SSPF-C, (SEQ ID NO:) was synthesized at Sigma-Genosys (Woodlands, Tex.). ELISA was performed as previously described (7).

Example 7

Construction of Bicistronic Reporter Vectors and the Reporter Assay

Three bicistronic reporter vectors were constructed: (1) the vector, DsRed-3'UTR-MPD6-IRES-EGFP (FIG. 3A-1); (2) the vector, DsRed-3'UTR-deleted MPD6-IRES-EGFP (FIG. 3A-2); and (3) DsRed-EMCV-IRES-EGFP (FIG. 3A-3). The reporter vector DsRed-EMCV-IRES-EGFP (FIG. 3A-3) was constructed by subcloning DsRed coding sequence (EcoRI-BamHI fragment) into the multiple cloning sites of the commercial bicistronic reporter vector pIRES2-EGFP (Clontech, Palo Alto, Calif.). The EcoRI-BamHI DsRed coding fragment was obtained by high-fidelity PCR (Clontech) using the DsRed-EcoRI mRNA sense primer specific for the 5' end of the DsRed ORF (Table 1) and the DsRed-BamHI antisense primer (Table 1). The reporter vector DsRed-3'UTR-MPD6-IRES-EGFP (FIG. 3A-1) was constructed by replacing EMCV-IRES with the 3'UTR-MPD6-IRES (BamHI-BstXI fragment), which was prepared by high-fidelity PCR using the sense primer specific for the 5' end of the myotrophin 3'UTR (Table 1) and the antisense primer specific for the 3' end of MPD6-IRES (Table 1). The reporter construct DsRed-3'UTR-deleted MPD6-IRES-EGFP (FIG. 3A-2) was constructed by replacing the EMCV-IRES fragment with the partially deleted 3'UTR-MPD6-IRES fragment in the pIRES2-EGFP vector. The deleted 3'UTR-MPD6-IRES fragment was prepared by high-fidelity PCR using the myotrophin 3'UTR mRNA sense primer to pair with the deleted BstXI antisense primer specific for the myotrophin 3'UTR region 600 by upstream of MPD6-IRES (Table 1). K562 cells were transfected using the X-tremeGENG Q2 Transfection Reagent (Roche, Diagnostics, Indianapolis, Ind.) with the above-described three bicistronic vectors, respectively. Stably transfected cells were selected by the resistance to the neomycin analog G418 (400 □ g/ml; Invitrogen). In order to detect the potential upregulation of DsRed and EGFP fluorescence induced by IFN-α and avoid the potential expression variation of individual transfected clones, we used transfected cells that are resistant to G418 for further experiments.

For IFN-α stimulation assay, transfected K562 cells and mock-transfected K562 control cells were treated with human IFN-α at a concentration of 1000 μm' for the time course of 0, 10, and 24 hours. The treated K562 cells were then washed with phosphate-buffered saline (PBS) twice. The expression of EGFP and DsRed was analyzed on a FACS-Calibur flow cytometer (Becton-Dickinson, San Jose, Calif.). Mock-transfected K562 cells were used for negative controls to set up the background gate. Data acquirement and analysis was performed using CellQuest Pro software (Becton-Dickinson). EGFP was measured in the FL1 channel (the green fluorescence at 508 nm) and DsRed, in the FL2 channel (the red fluorescence at 583 nm)(30).

Example 8

Western Blot

Western blot procedures were performed as described (7). Briefly, proteins in K562 cell lysates were loaded on gradient SDS-PAGE (Invitrogen, Carlsbad, Calif.), analyzed via Western blots with 1:1000 diluted eIF-2α antibody (Cell Signaling Technology, Beverly, Mass.), Phospho-eIF-2α (Ser51) Antibody (Cell Signaling), and anti-β-actin (1:2,000) (Santa Cruz Biotechnology, Santa Cruz, Calif.), respectively, and revealed by chemiluminescent substrate (Pierce Biotechnology, Rockford, Ill.) after exposure on X-ray film (Eastman Kodak, Rochester, N.Y.).

Example 9

Semi-Quantitative Reverse Transcription-PCR and PCR Cloning

Human IFN-α (1×105 Units/100 μ) was purchased from PBL Biomedical Laboratories, (Piscataway, N.J.). K562 cells (a human myeloid leukemia cell line purchased from American Type Culture Collection ATCC, Manassas, Va.) were cultured in RPMI 1640 medium (Invitrogen, Carlsbad, Calif.) supplemented with 10% fetal bovine serum in a humidified atmosphere of 5% carbon dioxide at 37° C. The K562 cells were stimulated with 1000 Units/ml of IFN-α for the time indicated (31). RNA preparation, RT-PCR, and PCR cloning were performed as previously described (32). A sense primer (PV1ORF5) specific for the 5' sequence of myotrophin-MPD6 and an antisense primer (PV1ORF3) specific for the 3' sequence of MPD6 were used for PCR (Table 1). The PCR with 25-35 cycles was used for semi-quantitation of MPD6 fragment. The 670 by PCR product was cloned into pCR4-TOPO vector (Invitrogen) and confirmed by DNA sequencing. As an internal control for cDNA preparation, the housekeeping gene β-actin was examined by PCR (sense primer HB-actin5 and anti-sense primer HB-actin3) (Table 1). The ethidium bromide staining signals of PCR products were analyzed with a documentation system (Eastman Kodak Company, Rochester, N.Y.) and normalized as relative densitometric units by comparing to β-actin amplified in the same cDNA preparations (32). ISG15, as a positive control for the genes upregulated by IFN-α stimulation (31), was amplified by PCR with a sense primer ISG5 and an antisense primer ISG3 (Table 1).

TABLE 1

| | | |
|---|---|---|
| MPD6 ORE5 | 5'-GCGCGAATTCCTTTTGTATTAATCAGTCATTTCA-:3' | (SEQ ID NO: 5) |
| MPD6 ORF3 | 5'-GCGCGAATTCTTACCATTCGGATGTACATGAACT-3' | (SEQ ID NO: 6) |
| MPD6RT5 | 5'-AGTGCCAGGGTGTTTTGA-3' | (SEQ ID NO: 7) |
| MPD6RT3 | 5'-TGAATGCAAGGGAGACTT-3' | (SEQ ID NO: 8) |
| ISG5 | 5'-GAGAGCAGCGAATTCATCT-3' | (SEQ ID NO: 9) |
| ISG3 | 5'-AAGGGGGACCCTGTCCTG-3' | (SEQ ID NO: 10) |
| HB-actin5 | 5'-ATCTGGCACCACACCTTTCTACATGAGCTGCG-3' | (SEQ ID NO: 11) |
| HB-actin3 | 5'-CGTCATACTCCTGCTTTGCTGATCCACATCTGC-3' | (SEQ ID NO: 12) |
| DsRed ORF5 | 5'-GGCGCGAATTCATGGCTCCTCCGAGACGTCA-:3' | (SEQ ID NO: 13) |
| DsRed.BamH13 | 5'-GGCGCGGATCCCTACAGGACAGGTGGTGGC-3' | (SEQ ID NO: 14) |
| Myotrophin 3'-UTR5 | 5'-GGCGCGGATCCGGATGGATGGACTGATAACTCC-3' | (SEQ ID NO: 15) |
| MPD6-IRES3 | 5'-GGCGCCCATGGTTGTGGACACTACAGAACATGCAT-3' | (SEQ ID NO: 16) |
| MPD6-IRESdel3 | 5'-GGCGCCCATGGTTGTGGAGAGTGCCTCCATTTTCAA-3' | (SEQ ID NO: 17) |

While the invention has been described in detail and with reference to specific examples thereof, it will be apparent to one skilled in the art that various changes and modifications can be made therein without departing from the spirit and scope thereof.

References

1. Belardelli, F., M. Ferrantini, E. Proietti, and J. M. Kirkwood. 2002. Interferon-alpha in tumor immunity and immunotherapy. Cytokine & Growth Factor Reviews 13:119-134.
2. Liu, E., J. Jelinek, Y. D. Pastore, Y. Guan, J. F. Prchal, and J. T. Prchal. 2003. Discrimination of polycythemias and thrombocytoses by novel, simple, accurate clonality assays and comparison with PRV-1 expression and BFU-E response to erythropoietin. Blood 101:3294-3301.
3. Lengfelder, E., U. Berger, and R. Hehlmann. 2000. Interferon alpha in the treatment of polycythemia vera. Ann Hematol 79:103-109.
4. Fujii, S. 2000. Role of interferon-alpha and clonally expanded T cells in the immunotherapy of chronic myelogenous leukemia. Leuk Lymphoma 38:21-38.
5. Sacchi, S., H. Kantarjian, S. O'Brien, P. R. Cohen, S. Pierce, and M. Talpaz. 1995. Immune-mediated and unusual complications during interferon alfa therapy in chronic myelogenous leukemia. J Clin Oncol 13:2401-2407.
6. Wu, C. J., X. F. Yang, S. McLaughlin, D. Neuberg, C. Canning, B. Stein, E. P. Alyea, R. J. Soiffer, G. Dranoff, and J. Ritz. 2000. Detection of a potent humoral response associated with immune-induced remission of chronic myelogenous leukemia. J Clin Invest 106:705-714.
7. Yang, X. F., C. J. Wu, S. McLaughlin, A. Chillemi, K. S. Wang, C. Canning, E. P. Alyea, P. Kantoff, R. J. Soiffer, G. Dranoff, and J. Ritz. 2001. CML66, a broadly immunogenic tumor antigen, elicits a humoral immune response associated with remission of chronic myelogenous leukemia. Proc Natl Acad Sci USA 98:7492-7497.
8. Yang, X. F., C. J. Wu, L. Chen, E. P. Alyea, C. Canning, P. Kantoff, R. J. Soiffer, G. Dranoff, and J. Ritz. 2002. CML28 is a broadly immunogenic antigen, which is overexpressed in tumor cells. Cancer Res 62:5517-5522.
9. Sahin, U., O. Tureci, H. Schmitt, B. Cochlovius, T. Johannes, R. Schmits, F. Stenner, G. Luo, I. Schobert, and M. Pfreundschuh. 1995. Human neoplasms elicit multiple specific immune responses in the autologous host. Proc Natl Acad Sci USA 92:11810-11813.
10. Wu, C. J., M. Biernacki, J. L. Kutok, S. Rogers, L. Chen, X. F. Yang, R. J. Soiffer, and J. Ritz. 2005. Graft-versusleukemia target antigens in chronic myelogenous leukemia are expressed on myeloid progenitor cells. Clin Cancer Res 11:4504-4511.
11. Yang, X.-F., Y. Yan, L. Phan, Z. Xiong, J. Jelinek, and J. Prchal. 2002. Upregulation of cancer-testis antigens in polycythemia vera cells suggests their potential role in immune responses against myeloproliferation. BLOOD 100:348b.
12. Chen, Y. 2004. SEREX review. Cancer Immunity http://www.cancerimmunity.org/SEREX/.
13. Jager, E., Y. Nagata, S. Gnjatic, H. Wada, E. Stockert, J. Karbach, P. R. Dunbar, S. Y. Lee, A. Jungbluth, D. Jager, M. Arand, G. Ritter, V. Cerundolo, B. Dupont, Y. T. Chen, L. J. Old, and A. Knuth. 2000. Monitoring CD8 T cell responses to NY-ESO-1: correlation of humoral and cellular immune responses. Proc Natl Acad Sci USA 97:4760-4765.
14. Yang, F., and X. F. Yang. 2005. New concepts in tumor antigens: their significance in future immunotherapies for tumors. Cell Mol 1 mmol 2:331-341.
15. Guilloux, Y., S. Lucas, V. G. Brichard, A. Van Pel, C. Viret, E. De Plaen, F. Brasseur, B. Lethe, F. Jotereau, and T. Boon. 1996. A peptide recognized by human cytolytic T lymphocytes on HLA-A2 melanomas is encoded by an intron sequence of the N-acetylglucosaminyltransferase V gene. J Exp Med 183:1173-1183.
16. Wang, R. F., M. R. Parkhurst, Y. Kawakami, P. F. Robbins, and S. A. Rosenberg. 1996. Utilization of an alternative open reading frame of a normal gene in generating a novel human cancer antigen. J Exp Med 183:1131-1140.
17. Schwab, S. R., J. A. Shugart, T. Homg, S. Malarkannan, and N. Shastri. 2004. Unanticipated Antigens Translation Initiation at CUG with Leucine. PLoS Biol 2:e366.
18. Malarkannan, S., T. Homg, P. P. Shih, S. Schwab, and N. Shastri. 1999. Presentation of out-of-frame peptide/MHC class I complexes by a novel translation initiation mechanism. Immunity 10:681-690.
19. Shastri, N., S. Schwab, and T. Serwold. 2002. Producing nature's gene-chips: the generation of peptides for display by MHC class I molecules. Annu Rev Immunol 20:463-493.
20. Yan, Y., L. Phan, F. Yang, M. Talpaz, Y. Yang, Z. Xiong, B. Ng, N. A. Timchenko, C. J. Wu. J. Ritz, H. Wang, and X. F. Yang. 2004. A novel mechanism of alternative promoter and splicing regulates the epitope generation of tumor antigen CML66-L. J Immunol 172:651-660.
21. Ng, B., Fan Yang, David P. Huston, Yan Yan, Yu Yang, Zeyu Xiong, Leif E. Peterson, Hong Wang, Xiao-Feng Yang. 2004. Increased non-canonical splicing of autoantigen transcripts provides the structural basis for expression of untolerized epitopes. J. Allergy and Clin. Immunol. December 2004.
22. Yang, F., I H Chen, Z Xiong, Y Yan, H Wang, X-F Yang. 2006. Model of stimulation-responsive splicing and strategies in identification of immunogenic isoforms of tumor antigens and autoantigens. Clinical Immunology in press.
23. Xiong, Z., Liu, E, Yan Y, Silver, R. T., Zhang, S, Yang, Y and S. Verstovsek, Yang, F, Chen, I. H., Segura, F. J., Wang, H, Prchal, J, Yang, X.-F. 2005. NOVEL UNCONVENTIONAL AND CONVENTIONAL ANTIGENS ELICIT ANTI-TUMOR HUMORAL IMMUNE REACTIONS IN A SUBSET OF PATIENTS WITH POLYCYTHEMIA VERA. Blood Submission.
24. Hellen, C. U., and P. Sarnow. 2001. Internal ribosome entry sites in eukaryotic mRNA molecules. Genes Dev 15:1593-1612.
25. Stoneley, M., and A. E. Willis. 2004. Cellular internal ribosome entry segments: structures, trans-acting factors and regulation of gene expression. Oncogene 23:3200-3207.
26. Gure, A. 0., 0. Tureci, U. Sahin, S. Tsang, M. J. Scanlan, E. Jager, A. Knuth, M. Pfreundschuh, L. J. Old, and Y. T. Chen. 1997. SSX: a multigene family with several members transcribed in normal testis and human cancer. Int J Cancer 72:965-971.
27. Mignone, F., G. Grillo, F. Licciulli, M. Iacono, S. Liuni, P. J. Kersey, J. Duarte, C. Saccone, and G. Pesole. 2005. UTRdb and UTRsite: a collection of sequences and regulatory motifs of the untranslated regions of eukaryotic mRNAs. Nucleic Acids Res 33:D141-146.
28. Zuker, M. 2003. Mfold web server for nucleic acid folding and hybridization prediction. Nucleic Acids Res 31:3406-3415.
29. Hofacker, I. L. 2003. Vienna RNA secondary structure server. Nucleic Acids Res 31:3429-3431.
30. Hawley, T. S., W. G. Telford, A. Ramezani, and R. G. Hawley. 2001. Four-color flow cytometric detection of retrovirally expressed red, yellow, green, and cyan fluorescent proteins. Biotechniques 30:1028-1034.
31. Smith, J. K., A. A. Siddiqui, G. A. Krishnaswamy, R. Dykes, S. L. Berk, M. Magee, W. Joyner, and J. Cummins. 1999. Oral use of interferon-alpha stimulates ISG-15 transcription and production by human buccal epithelial cells. J Interferon Cytokine Res 19:923-928.
32. Yang, X. F., G. F. Weber, and H. Cantor. 1997. A novel Bcl-x isoform connected to the T cell receptor regulates apoptosis in T cells. Immunity 7:629-639.
33. Streilein, J. W. 1995. Unraveling immune privilege. Science 270:1158-1159.
34. Chen, Y. T. 2000. Cancer vaccine: identification of human tumor antigens by SEREX [In Process Citation]. Cancer J Sci Am 6 Suppl 3:S208-217.
35. Hoeppner, L. H., J. A. Dubovsky, E. J. Dunphy, and D. G. McNeel. 2006. Humoral immune responses to testis antigens in sera from patients with prostate cancer. Cancer Immun 6:1.
36. Okada, T., M. Akada, T. Fujita, T. Iwata, Y. Goto, K. Kido, T. Okada, Y. Matsuzaki, K. Kobayashi, S. Matsuno, M. Sunamura, and Y. Kawakami. 2006. A novel cancer testis antigen that is frequently expressed in pancreatic, lung, and endometrial cancers. Clin Cancer Res 12:191-197.
37. Sivasubramanian, N., G. Adhikary, P. C. Sil, and S. Sen. 1996. Cardiac myotrophin exhibits rel/NF-kappa B interacting activity in vitro. J Biol Chem 271:2812-2816.
38. Gupta, S., and S. Sen. 2002. Myotrophin-kappaB DNA interaction in the initiation process of cardiac hypertrophy. Biochim Biophys Acta 1589:247-260.
39. Knuefermann, P., P. Chen, A. Misra, S. P. Shi, M. Abdellatif, and N. Sivasubramanian. 2002. Myotrophin/V-1, a protein up-regulated in the failing human heart and in postnatal cerebellum, converts NFkappa B p50-p65 heterodimers to p50-p50 and p65-p65 homodimers. J Biol Chem 277:23888-23897.
40. Bullock, T. N., A. E. Patterson, L. L. Franlin, E. Notidis, and L. C. Eisenlohr. 1997. Initiation codon scanthrough versus termination codon readthrough demonstrates strong potential for major histocompatibility complex class I-restricted cryptic epitope expression. J Exp Med 186:1051-1058.
41. Liu, H. X., L. Cartegni, M. Q. Zhang, and A. R. Krainer. 2001. A mechanism for exon skipping caused by nonsense or missense mutations in BRCA1 and other genes. Nat Genet 27:55-58.

42. Kozak, M. 1996. Interpreting cDNA sequences: some insights from studies on translation. Mamm Genome 7:563-574.
43. Shastri, N., V. Nguyen, and F. Gonzalez. 1995. Major histocompatibility class I molecules can present cryptic translation products to T-cells. J Biol Chem 270:1088-1091.
44. Aubsubel, F., Brent, R, Kingston, R E, Moore, D D, Seidman, J G, Smith, J A, and Struhl, K. 1999. Screening of Recombinant DNA Libraries In Current Protocols in Molecular Biology. V. Chanda, ed. John Wiley & Sons, Inc. A.1C.3.
45. Landschulz, W. H., P. F. Johnson, and S. L. McKnight. 1988. The leucine zipper: a hypothetical structure common to a new class of DNA binding proteins. Science 240:1759-1764.
46. Furuno, M., T. Kasukawa, R. Saito, J. Adachi, H. Suzuki, R. Baldarelli, Y. Hayashizaki, and Y. Okazaki. 2003. CDS annotation in full-length cDNA sequence. Genome Res 13:1478-1487.
47. Jameson, B. A., and H. Wolf. 1988. The antigenic index: a novel algorithm for predicting antigenic determinants. Comput Appi Biosci 4:181-186.
48. Mahler, M., M. Bluthner, and K. M. Pollard. 2003. Advances in B-cell epitope analysis of autoantigens in connective tissue diseases. Clin Immunol 107:65-79.
49. Preuss, K. D., C. Zwick, C. Bormann, F. Neumann, and M. Pfreundschuh. 2002. Analysis of the B-cell repertoire against antigens expressed by human neoplasms. Immunol Rev 188:43-50.
50. Komar, A. A., and M. Hatzoglou. 2005. Internal ribosome entry sites in cellular mRNAs: mystery of their existence. J Biol Chem 280:23425-23428.
51. Holcik, M., C. Lefebvre, C. Yeh, T. Chow, and R. G. Korneluk. 1999. A new internal-ribosome-entry-site motif potentiates XIAP-mediated cytoprotection. Nat Cell Biol 1:190-192.
52. Hennecke, M., M. Kwissa, K. Metzger, A. Oumard, A. Kroger, R. Schirmbeck, J. Reimann, and H. Hauser. 2001. Composition and arrangement of genes define the strength of IRES-driven translation in bicistronic mRNAs. Nucleic Acids Res 29:3327-3334.
53. Kraunus, J., D. H. Schaumann, J. Meyer, U. Modlich, B. Fehse, G. Brandenburg, D. von Laer, H. Klump, A. Schambach, J. Bohne, and C. Baum. 2004. Self-inactivating retroviral vectors with improved RNA processing. Gene Ther 11:1568-1578.
54. Kralovics, R., D. W. Stockton, and J. T. Prchal. 2003. Clonal hematopoiesis in familial polycythemia vera suggests the involvement of multiple mutational events in the early pathogenesis of the disease. Blood 102:3793-3796.
55. Bhattachary-Chatterjee, M., R. Nath Baral, S. K. Chatterjee, R. Das, H. Zeytin, M. Chakraborty, and K. A. Foon. 2000. Counterpoint. Cancer vaccines: single-epitope anti-idiotype vaccine versus multiple-epitope antigen vaccine. Cancer Immunol Immunother 49:133-141.
56. Levine, R. L., M. Wadleigh, J. Cools, B. L. Ebert, G. Wernig, B. J. Huntly, T. J. Boggon, I. Wlodarska, J. J. Clark, S. Moore, J. Adelsperger, S. Koo, J. C. Lee, S. Gabriel, T. Mercher, A. D'Andrea, S. Frohling, K. Dohner, P. Marynen, P. Vandenberghe, R. A. Mesa, A. Tefferi, J. D. Griffin, M. J. Eck, W. R. Sellers, M. Meyerson, T. R. Golub, S. J. Lee, and D. G. Gilliland. 2005. Activating mutation in the tyrosine kinase JAK2 in polycythemia vera, essential thrombocythemia, and myeloid metaplasia with myelofibrosis. Cancer Cell 7:387-397.
57. Kralovics, R., F. Passamonti, A. S. Buser, S. S. Teo, R. Tiedt, J. R. Passweg, A. Tichelli, M. Cazzola, and R. C. Skoda. 2005. A gain-of-function mutation of JAK2 in myeloproliferative disorders. N Engl J Med 352:1779-1790.
58. Zhao, R., S. Xing, Z. Li, X. Fu, Q. Li, S. B. Krantz, and Z. J. Zhao. 2005. Identification of an acquired JAK2 mutation in polycythemia vera. J Biol Chem 280:22788-22792.
59. James, C., V. Ugo, J. P. Le Couedic, J. Staerk, F. Delhommeau, C. Lacout, L. Garcon, H. Raslova, R. Berger, A. Bennaceur-Griscelli, J. L. Villeval, S, N. Constantinescu, N. Casadevall, and W. Vainchenker. 2005. A unique clonal JAK2 mutation leading to constitutive signalling causes polycythaemia vera. Nature 434:1144-1148.
60. Baxter, E. J., L. M. Scott, P. J. Campbell, C. East, N. Fourouclas, S. Swanton, G. S. Vassiliou, A. J. Bench, E. M. Boyd, N. Curtin, M. A. Scott, W. N. Erber, and A. R. Green. 2005. Acquired mutation of the tyrosine kinase JAK2 in human myeloproliferative disorders. Lancet 365:1054-1061.
61. Verma, A., S. Kambhampati, S. Parmar, and L. C. Platanias. 2003. Jak family of kinases in cancer. Cancer Metastasis Rev 22:423-434.
62. Jager, D., C. Taverna, A. Zippelius, and A. Knuth. 2004. Identification of tumor antigens as potential target antigens for immunotherapy by serological expression cloning. Cancer Immunol Immunother 53:144-147.
63. Ehlken, H., D. Schadendorf, and S. Eichmuller. 2004. Humoral immune response against melanoma antigens induced by vaccination with cytokine gene-modified autologous tumor cells. Int J Cancer 108:307-313.
64. Okada, H., J. Attanucci, K. M. Giezeman-Smits, C. Brissette-Storkus, W. K. Fellows, A. Gambotto, L. F. Pollack, K. Pogue-Geile, M. T. Lotze, M. E. Bozik, and W. H. Chambers. 2001. Immunization with an antigen identified by cytokine tumor vaccine-assisted SEREX (CAS) suppressed growth of the rat 9L glioma in vivo. Cancer Res 61:2625-2631.
65. Ono, T., S. Sato, N. Kimura, M. Tanaka, A. Shibuya, L. J. Old, and E. Nakayama. 2000. Serological analysis of BALB/C methylcholanthrene sarcoma meth A by SEREX: identification of a cancer/testis antigen [In Process Citation]. Int J Cancer 88:845-851.
66. Schwab, S. R., K. C. Li, C. Kang, and N. Shastri. 2003. Constitutive display of cryptic translation products by MHC class I molecules. Science 301:1367-1371.
67. Molldrem, J. J., P. P. Lee, C. Wang, K. Felio, H. M. Kantarjian, R. E. Champlin, and M. M. Davis. 2000. Evidence that specific T lymphocytes may participate in the elimination of chronic myelogenous leukemia. Nat Med 6:1018-1023.
68. Gilbert, H. S. 2001. Current management in polycythemia vera. Semin Hematol 38:25-28.
69. Certa, U., M. Wilhelm-Seiler, S. Foser, C. Broger, and M. Neeb. 2003. Expression modes of interferon-alpha inducible genes in sensitive and resistant human melanoma cells stimulated with regular and pegylated interferon-alpha. Gene 315:79-86.
70. Baechler, E. C., F. M. Batliwalla, G. Karypis, P. M. Gaffney, W. A. Ortmann, K. J. Espe, K. B. Shark, W. J. Grande, K. M. Hughes, V. Kapur, P. K. Gregersen, and T. W. Behrens. 2003. Interferon-inducible gene expression signature in peripheral blood cells of patients with severe lupus. Proc Natl Acad Sci USA 100:2610-2615.
71. Ng, B., F. Yang, D. P. Huston, Y. Yan, Y. Yang, Z. Xiong, L. E. Peterson, H. Wang, and X. F. Yang. 2004. Increased noncanonical splicing of autoantigen transcripts provides the structural basis for expression of untolerized epitopes. J Allergy Clin Immunol 114:1463-1470.
72. Ludewig, B., T. Junt, H. Hengartner, and R. M. Zinkernagel. 2001. Dendritic cells in autoimmune diseases. Curr Opin Immunol 13:657-662.
73. Zinkernagel, R. M., and H. Hengartner. 2001. Regulation of the immune response by antigen. Science 293:251-253.
74. Bauer, C., I. Diesinger, N. Brass, H. Steinhart, H. Iro, and E. U. Meese. 2001. Translation initiation factor eIF-4G is immunogenic, overexpressed, and amplified in patients with squamous cell lung carcinoma. Cancer 92:822-829.
75. Nagata, Y., S. Ono, M. Matsuo, S. Gnjatic, D. Valmori, G. Ritter, W. Garrett, L. J. Old, and I. Mellman. 2002. Differential presentation of a soluble exogenous tumor antigen, NY-ESO-1, by distinct human dendritic cell populations. Proc Natl Acad Sci USA 99:10629-10634.
76. Steinman, R. M., K. Inaba, S. Turley, P. Pierre, and I. Mellman. 1999. Antigen capture, processing, and presentation by dendritic cells: recent cell biological studies. Hum Immunol 60:562-567.
77. Davidoff, A. M., J. D. Iglehart, and J. R. Marks. 1992. Immune response to p53 is dependent upon p53/HSP70 complexes in breast cancers. Proc Natl Acad Sci USA 89:3439-3442.
78. Thery, C., M. Boussac, P. Veron, P. Ricciardi-Castagnoli, G. Raposo, J. Garin, and S. Amigorena. 2001. Proteomic analysis of dendritic cell-derived exosomes: a secreted subcellular compartment distinct from apoptotic vesicles. J Immunol 166:7309-7318.
79. Moudgil, K., and Sercarz, E E. 1998. Antigenic determinants involved in induction and propagation of autoimmunity. In The Autoimmune Diseases, 3rd ed. N. Rose, and Mackay, I R, ed. Academic Press, San Diego, London, Boston, New York, Sydney, Tokyo, Toronto. 45-58.
80. Simpson, E., D. Scott, and P. Chandler. 1997. The male-specific histocompatibility antigen, H-Y: a history of transplantation, immune response genes, sex determination and expression cloning. Annu Rev Immunol 15:39-61.
81. Talpaz, M., Ravandi, F, Kurzrock, R, Estrov, Z, Kantarjian, H M. 2000. Interferon-a and b: Clinical application. Lippincott Williams & Wilkins, Philadelphia, Baltimore, New York, London, Buenos Aires, HongKong, Sydney, Tokyo.
82. Bonnal, S., C. Boutonnet, L. Prado-Lourenco, and S. Vagner. 2003. IRESdb: the Internal Ribosome Entry Site database. Nucleic Acids Res 31:427-428.
83. Stoneley, M., S. A. Chappell, C. L. Jopling, M. Dickens, M. MacFarlane, and A. E. Willis. 2000. c-Myc protein synthesis is initiated from the internal ribosome entry segment during apoptosis. Mol Cell Biol 20:1162-1169.
84. Kobayashi, N., K. Saeki, and A. Yuo. 2003. Granulocyte-macrophage colony-stimulating factor and interleukin-3 induce cell cycle progression through the synthesis of c-Myc protein by internal ribosome entry site-mediated translation via phosphatidylinositol 3-kinase pathway in human factor-dependent leukemic cells. Blood 102:3186-3195.
85. Holcik, M., N. Sonenberg, and R. G. Korneluk. 2000. Internal ribosome initiation of translation and the control of cell death. Trends Genet. 16:469-473.
86. Rivas-Estilla, A. M., Y. Svitkin, M. Lopez Lastra, M. Hatzoglou, A. Sherker, and A. E. Koromilas. 2002. PKR-dependent mechanisms of gene expression from a subgenomic hepatitis C virus clone. J Virol 76:10637-10653.
87. Stark, G. R., I. M. Kerr, B. R. Williams, R. H. Silverman, and R. D. Schreiber. 1998. How cells respond to interferons. Annu Rev Biochem 67:227-264.

---

What is claimed is:

1. A substantially purified polypeptide of SEQ ID NO: 2, and fragments thereof.

2. An immunogenic peptide of SEQ ID NO: 2, and fragments thereof.

3. A kit comprising an immunogenic peptide of SEQ ID NO: 2, and fragments thereof.

* * * * *

SEQUENCE LISTING

```
<160> NUMBER OF SEQ ID NOS: 20

<210> SEQ ID NO 1
<211> LENGTH: 1096
<212> TYPE: DNA
<213> ORGANISM: Homo sapiens

<400> SEQUENCE: 1
accatgtgat tctttgtaca gtttatcctg atgttgcttg taatgcagta gaggctattt      60
cgccttcgct tttctttctc gacctttttg taaaccctat aattatgaag cgattgcttg     120
agaaaataac atataaacat agaatagaat agactgacca agatggttca cagtttcttt     180
ttttaactag gttatttata atgtatttct gaaccacttg gcagacaaat tcacaacact     240
taatgttcat attttgagta aaggaagcta aaaccatgtt tgctttctgg tactacatgc     300
attagcgaaa ggttaagtaa gttttgttct ccactgaagt aatacttaac atctcagaaa     360
aaattttgca tgttctgtag ttttgtatta aatcagtcat ttcatatgca ctatatcaag     420
tacaaacagg tagtttacct gtttatagta gtgtactaac aaagtctccc ttgcagcttc     480
agactgttat ctataggctt atcgttcaaa tacagcactt gaatatccca agtagttctt     540
ctacgcatag ctcacctttc taaacccagt taagcatgga agagaggtag taggtaggtg     600
cagtgtgtgg aagctgcaaa caagtaggcc ttttattcat tgatatcttt tcccaagtac     660
tggattttaa atctgtatgt atctgtttga ttttttttc taatatttca gttgagctgc      720
tgttttcttc catgcaatat tgtatactca attgtgtata gaagaagctg gtgagagtgc     780
```

```
cctcctacat aaataagcaa ttgcagtgtt ttgcatgcaa aatataaaaa atttaaattg      840
tcctgattct attttgtaaa tggagaaaca atcatatctt tctaagcggt aatggaggaa      900
gactagtgct ttgtgcattt tgatatattt gagttcattt tttccacaat gtcatacttt      960
tgacgcagtt gggtttctca taagtatcct agttcatgta catccgaatg ctaaataata      1020
ctgtgtttta agtttgtgt tgcaagaaca aatggaataa acttgaattg tgctacgaaa      1080
aaaaaaaaaa aaaaaa                                                    1096
```

<210> SEQ ID NO 2
<211> LENGTH: 58
<212> TYPE: PRT
<213> ORGANISM: Homo sapiens

<400> SEQUENCE: 2

```
Met Lys Ser Val Ile Ser Tyr Ala Leu Tyr Gln Val Gln Thr Gly Ser
1               5                   10                  15

Leu Pro Val Tyr Ser Ser Val Leu Thr Lys Ser Pro Leu Gln Leu Gln
            20                  25                  30

Thr Val Ile Tyr Arg Leu Ile Val Gln Ile Gln His Leu Asn Ile Pro
        35                  40                  45

Ser Ser Ser Ser Thr His Ser Ser Pro Phe
    50                  55
```

<210> SEQ ID NO 3
<211> LENGTH: 20
<212> TYPE: PRT
<213> ORGANISM: Homo sapiens

<400> SEQUENCE: 3

```
Ile Val Gln Ile Gln His Leu Asn Ile Pro Ser Ser Ser Ser Thr His
1               5                   10                  15

Ser Ser Pro Phe
            20
```

<210> SEQ ID NO 4
<211> LENGTH: 35
<212> TYPE: DNA
<213> ORGANISM: Homo sapiens

<400> SEQUENCE: 4

```
ggcgcgaatt cctttgtat taatcagtca tttca                                 35
```

<210> SEQ ID NO 5
<211> LENGTH: 35
<212> TYPE: DNA
<213> ORGANISM: Homo sapiens

<400> SEQUENCE: 5

```
ggcgcgaatt cttaccattc ggatgtacat gaact                                35
```

<210> SEQ ID NO 6
<211> LENGTH: 18
<212> TYPE: DNA
<213> ORGANISM: Homo sapiens

<400> SEQUENCE: 6

```
agtgccaggg tgttttga                                                   18
```

<210> SEQ ID NO 7
<211> LENGTH: 18

```
<212> TYPE: DNA
<213> ORGANISM: Homo sapiens

<400> SEQUENCE: 7
tgaatgcaag ggagactt                                               18

<210> SEQ ID NO 8
<211> LENGTH: 19
<212> TYPE: DNA
<213> ORGANISM: Homo sapiens

<400> SEQUENCE: 8
gagagcagcg aattcatct                                              19

<210> SEQ ID NO 9
<211> LENGTH: 18
<212> TYPE: DNA
<213> ORGANISM: Homo sapiens

<400> SEQUENCE: 9 aaggggggacc ctgtcctg                                              18

<210> SEQ ID NO 10
<211> LENGTH: 31
<212> TYPE: DNA
<213> ORGANISM: Homo sapiens

<400> SEQUENCE: 10
atctggcacc acccttcta catgagctgc g                                 31

<210> SEQ ID NO 11
<211> LENGTH: 32
<212> TYPE: DNA
<213> ORGANISM: Homo sapiens

<400> SEQUENCE: 11
cgtcatactc ctgcttgctg atccacatct gc                               32

<210> SEQ ID NO 12
<211> LENGTH: 31
<212> TYPE: DNA
<213> ORGANISM: Homo sapiens

<400> SEQUENCE: 12
ggcgcgaatt catggctcct ccgagacgtc a                                31

<210> SEQ ID NO 13
<211> LENGTH: 30
<212> TYPE: DNA
<213> ORGANISM: Homo sapiens

<400> SEQUENCE: 13
ggcgcggatc cctacaggac aggtggtggc                                  30

<210> SEQ ID NO 14
<211> LENGTH: 33
<212> TYPE: DNA
<213> ORGANISM: Homo sapiens

<400> SEQUENCE: 14
ggcgcggatc cggatggatg gactgataac tcc                              33

<210> SEQ ID NO 15
<211> LENGTH: 35
```

```
<212> TYPE: DNA
<213> ORGANISM: Homo sapiens

<400> SEQUENCE: 15
ggcgcccatg gttgtggaca ctacagaaca tgcat                               35

<210> SEQ ID NO 16
<211> LENGTH: 36
<212> TYPE: DNA
<213> ORGANISM: Homo sapiens

<400> SEQUENCE: 16
ggcgcccatg gttgtggaga gtgcctccat tttcaa                              36

<210> SEQ ID NO 17
<211> LENGTH: 58
<212> TYPE: PRT
<213> ORGANISM: Homo sapiens

<400> SEQUENCE: 17

Ile Lys Ser Val Ile Ser Tyr Ala Leu Tyr Gln Val Gln Thr Gly Ser
1               5                   10                  15

Leu Pro Val Tyr Ser Ser Val Leu Thr Lys Ser Pro Leu Gln Leu Gln
            20                  25                  30

Thr Val Ile Tyr Arg Leu Ile Val Gln Ile Gln His Leu Asn Ile Pro
        35                  40                  45

Ser Ser Ser Ser Thr His Ser Ser Pro Phe
    50                  55

<210> SEQ ID NO 18
<211> LENGTH: 58
<212> TYPE: PRT
<213> ORGANISM: Homo sapiens

<400> SEQUENCE: 18

Ile Lys Ser Val Ile Ser Tyr Ala Leu Tyr Gln Val Gln Thr Gly Ser
1               5                   10                  15

Leu Pro Val Tyr Ser Ser Val Leu Thr Lys Ser Pro Leu Gln Leu Gln
            20                  25                  30

Thr Val Ile Tyr Arg Leu Ile Val Gln Ile Gln His Leu Asn Ile Pro
        35                  40                  45

Ser Ser Ser Ser Thr His Ser Ser Pro Phe
    50                  55

<210> SEQ ID NO 19
<211> LENGTH: 6
<212> TYPE: DNA
<213> ORGANISM: Artificial
<220> FEATURE:
<223> OTHER INFORMATION: Kozak Consensus Sequence
<220> FEATURE:
<221> NAME/KEY: misc_feature
<222> LOCATION: (2)..(3)
<223> OTHER INFORMATION: n is a, c, g, or t

<400> SEQUENCE: 19 annagg                                                               6

<210> SEQ ID NO 20
<211> LENGTH: 6
<212> TYPE: DNA
<213> ORGANISM: Artificial
<220> FEATURE:
<223> OTHER INFORMATION: Kozak Consensus Sequence
```

```
<220> FEATURE:
<221> NAME/KEY: misc_feature
<222> LOCATION: (2)..(3)
<223> OTHER INFORMATION: n is a, c, g, or t

<400> SEQUENCE: 20 gnnagg                                                                    6
```